(12) United States Patent
Stauffer

(10) Patent No.: US 8,143,405 B2
(45) Date of Patent: Mar. 27, 2012

(54) PIPERIDINE AND PYRROLIDINE BETA-SECRETASE INHIBITORS FOR THE TREATMENT OF ALZHEIMER'S DISEASE

(75) Inventor: Shaun R. Stauffer, Schwenksville, PA (US)

(73) Assignee: Merck, Sharp & Dohme Corp, Rahway, NJ (US)

( * ) Notice: Subject to any disclaimer, the term of this patent is extended or adjusted under 35 U.S.C. 154(b) by 316 days.

(21) Appl. No.: 12/311,158

(22) PCT Filed: Sep. 19, 2007

(86) PCT No.: PCT/US2007/020303
§ 371 (c)(1),
(2), (4) Date: Mar. 20, 2009

(87) PCT Pub. No.: WO2008/036316
PCT Pub. Date: Mar. 27, 2008

(65) Prior Publication Data
US 2010/0041667 A1    Feb. 18, 2010

Related U.S. Application Data

(60) Provisional application No. 60/846,400, filed on Sep. 21, 2006.

(51) Int. Cl.
C07D 405/00 (2006.01)
C07D 271/10 (2006.01)
(52) U.S. Cl. .......................... 546/210; 548/143
(58) Field of Classification Search .................. 546/210; 548/143
See application file for complete search history.

(56) References Cited

U.S. PATENT DOCUMENTS

| | | | |
|---|---|---|---|
| 7,109,217 B2 | 9/2006 | Coburn et al. |
| 7,115,652 B2 | 10/2006 | Yang |
| 7,132,568 B2 | 11/2006 | Yang et al. |
| 7,291,620 B2 | 11/2007 | Coburn et al. |
| 7,348,448 B2 | 3/2008 | Nantermet et al. |
| 7,354,942 B2 | 4/2008 | Nantermet et al. |
| 2006/0293380 A1 | 12/2006 | Nantermet et al. |
| 2007/0142634 A1 | 6/2007 | Barrow et al. |
| 2008/0039474 A1 | 2/2008 | Rosenblum et al. |

FOREIGN PATENT DOCUMENTS

| | | |
|---|---|---|
| WO | WO03/043987 | 5/2003 |
| WO | WO2004/043916 | 5/2004 |
| WO | WO2004/101512 | * 11/2004 |
| WO | WO2005/032550 | * 4/2005 |
| WO | WO 2005/103020 A1 | 11/2005 |
| WO | WO 2005/103043 A1 | 11/2005 |
| WO | WO2006/002004 | 1/2006 |
| WO | WO 2006/002004 A1 | 1/2006 |
| WO | WO2006/069155 | * 6/2006 |
| WO | WO2008/011130 | * 1/2008 |

OTHER PUBLICATIONS

Alfred Burger, Isosterism and Bioisosterism in Drug Design, in Progress in Drug Research 287-328 (Ernst Jucker, ed., Birkhauser Verlag, 1991).*
George Patani & Edmond LaVoie, Bioisosterism: A Rational Approach in Drug Design, 96 Chem. Rev. 3147 (1996).*
Daisuke Shuto, et al, KMI-008, A Novel B-Secretase Inhibitor Containing a Hydroxymethylcarbonyl Isostere as a Transition-State Mimic: Design and Synthesis of Substrate-Based Octapeptides, 13 Bioorg. Med. Chem. Let. 4273 (2003).*
Craig Coburn, et al, Identification of a Small Molecule Nonpeptide Active Site B-Secretase Inhibitor that Displaysa Nontraditional Binding Mode for Aspartyl Proteases, 47 J Med. Chem. 6117 (2004).*
Shawn Satchel, et al, Structure-Based Design of Potent and Selective Cell-Permeable Inhibitors of Human B-Secretase (BAC-1), 47 J Med. Chem. 6447 (2004).*
Shawn Satchel, et al, Conformationally Biased P3 Amide Replacements of B-Secretase Inhibitors, 16 Bioorg. Med. Chem. Let. 641 (2006).*
Martin Citron, B-Secretase Inhibitor for the Treatment of Alzheimer's Disease—Promise and Challenge,25 Trends Pharmacol. Sci. 92 (Feb. 2004).*
Jeffrey-Tri Nguyen, et al, Views on Amyloid Hypothesis and Secretase Inhibitors for Treating Alzheimer's Disease: Progress and Problems, 12 Curr. Pharma. Design 4295 (2006).*
European Search Report and Opinion for EP App. No. 07838507.7 corresponding to PCT/US2007/020303; dated Nov. 5, 2010; 5 pages.
International Preliminary Report on Patentability for PCT/US2008/036316, dated Nov. 6, 2008.

* cited by examiner

Primary Examiner — Karlheinz R Skowronek
Assistant Examiner — Sean Basquill
(74) Attorney, Agent, or Firm — Keith D. MacMillan; Gerard M. Devlin

(57) ABSTRACT

The present invention is directed to compounds of formula (I)

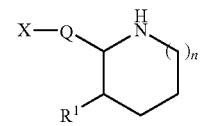

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

21 Claims, No Drawings

PIPERIDINE AND PYRROLIDINE BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) of U.S. provisional application Ser. No. 60/846,400, filed Sep. 21, 2006.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to piperidine and pyprolidine compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein ($\beta$A4, also referred to as A$\beta$, $\beta$-protein and $\beta$AP) which is a proteolytic product of a precursor protein of much larger size. The amyloid precursor protein (APP or A$\beta$PP) has a receptor-like structure with a large ectodomain, a membrane spanning region and a short cytoplasmic tail. The A$\beta$ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative $\alpha$-secretase which cleaves within the A$\beta$ protein to release $\alpha$-$APP_S$ and precludes the release of intact A$\beta$. A minor portion of $APP_S$ is released by a $\beta$-secretase ("$\beta$-secretase"), which cleaves near the $NH_2$-terminus of APP and produces COOH-terminal fragments (CTFs) which contain the whole A$\beta$ domain.

Thus, the activity of $\beta$-secretase or $\beta$-site amyloid precursor protein-cleaving enzyme ("BACE") leads to the cleavage of APP, production of A$\beta$, and accumulation of $\beta$ amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit $\beta$-secretase or BACE may be useful for the treatment of Alzheimer's disease.

The compounds of the present invention are useful for treating Alzheimer's disease by inhibiting the activity of $\beta$-secretase or BACE, thus preventing the formation of insoluble A$\beta$ and arresting the production of A$\beta$.

SUMMARY OF THE INVENTION

The present invention is directed to compounds of general formula (I)

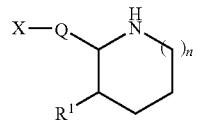

and individual enantiomers and diasteroisomers thereof, and pharmaceutically acceptable salts thereof, which are useful as inhibitors of the $\beta$-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the $\beta$-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to piperidine and pyrrolidine compounds represented by general formula (I)

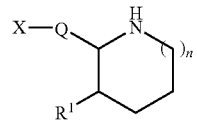

wherein
n is 0 or 1;
$R^1$ is (1) aryl selected from the group consisting of phenyl and napthyl,
  (2) heteroaryl,
  (3) —$C_{1-10}$ alkyl, and
  (4) $C_{3-8}$ cycloalkyl, said cycloalkyl optionally fused to a $C_{6-10}$ aryl group,
  wherein said alkyl, cycloalkyl, aryl or heteroaryl $R^1$ group is unsubstituted or substituted
  with one or more
  (a) halo,
  (b) —$C_{1-10}$ alkyl, wherein said alkyl is optionally substituted with halogen,
  (c) —OH,
  (d) —CN,
  (e) —O—$C_{1-10}$ alkyl,
  (f) —$C_{3-12}$ cycloalkyl, and
  (g) —$NR^AR^B$;
  wherein $R^A$ and $R^B$ are selected from the group consisting of
    (a) hydrogen,
    (b) —$C_{1-10}$ alkyl, and
    (c) —$C_{1-10}$ alkyl-$C_{6-10}$ aryl;

Q is selected from the group consisting of (1) 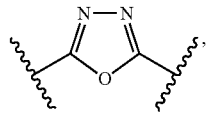, (2) —CH$_2$—O—C(=O)—,
(3) —CH$_2$—O—CH$_2$—,
(4) —CH$_2$—NH—CH$_2$—,
(5) —C(=O)—NH—CH$_2$—, and
(6) —CH$_2$—NH—C(=O)—;

X is selected from the group consisting of (1) 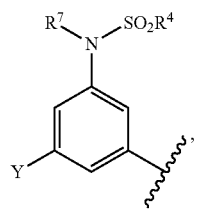

(2) 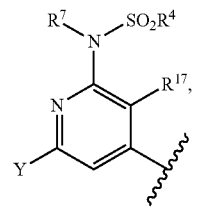

(3) 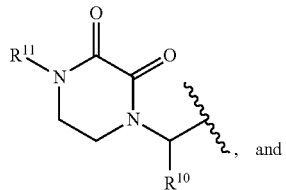, and (4) 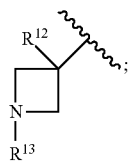;

Y is selected from the group consisting of
(1) —NR$^5$R$^6$,
(2) —C(=O)—NR$^5$R$^6$, (3) 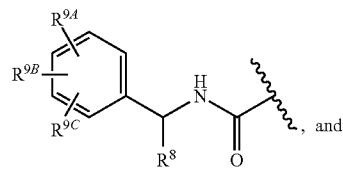, and (4) halogen;

R$^4$ is selected from the group consisting of
(1) —C$_{1-10}$ alkyl, or
(2) —C$_{3-12}$ cycloalkyl,
wherein said alkyl and cycloalkyl is optionally substituted with one or more
(a) halo,
(b) —OH,
(c) —CN,
(d) —O—C$_{1-10}$ alkyl,
(e) —C$_{1-10}$ alkyl,
(f) —C$_{3-12}$ cycloalkyl,
(g) aryl selected from the group consisting of phenyl and napthyl, or
(h) heteroaryl,
and said aryl and heteroaryl is optionally substituted with one or more
(i) halo,
(ii) —OH,
(iii) —CN,
(iv) —O—C$_{1-10}$ alkyl,
(v) —C$_{3-12}$ cycloalkyl, or
(vi) —C$_{1-10}$ alkyl;

R$^7$ is selected from the group consisting of
(1) hydrogen,
(2) —C$_{1-10}$ alkyl, and
(3) aryl selected from the group consisting of phenyl and naphthyl,
wherein said alkyl and aryl is optionally substituted with one or more
(a) halo,
(b) —OH,
(c) —CN,
(d) —O—C$_{1-10}$ alkyl,
(e) —C$_{3-12}$ cycloalkyl,
(f) aryl selected from the group consisting of phenyl and napthyl, or
(g) heteroaryl,
wherein said cycloalkyl, aryl or heteroaryl is optionally substituted with one or more
(i) halo,
(ii) —OH,
(iii) —CN,
(iv) —O—C$_{1-10}$ alkyl,
(v) —C$_{3-12}$ cycloalkyl, or
(vi) aryl selected from the group consisting of phenyl and napthyl;
or R$^4$ and R$^7$ may be linked to form a —CH$_2$CH$_2$CH$_2$— group;

R$^5$ and R$^6$ are independently selected from the group consisting of
(1) hydrogen,
(2) —C$_{1-10}$ alkyl,
(3) —C$_{2-10}$ alkenyl,
(4) —C$_{2-10}$ alkynyl, and
(5) —C$_{1-10}$ alkyl-C$_{3-12}$ cycloalkyl,
wherein said alkyl, cycloalkyl, alkenyl or alkynyl R$^5$ or R$^6$ group is optionally substituted with one or more
(a) halo,
(b) —OH,
(c) —CN,
(d) —C$_{1-10}$ alkyl
(e) —C$_{3-12}$ cycloalkyl,
(f) —O—C$_{1-10}$ alkyl, (g) heteroaryl, wherein said heteroaryl is optionally substituted with halogen;
(h) phenyl,
(i) —$NR^A R^B$,
(j) —C(=O)—$NR^A R^B$, or
(k) —C(=O)—OH,
or $R^5$ and $R^6$ are joined together with the nitrogen atom to which they are attached to form a 4-6 membered ring, which is optionally substituted with one or more
(a) —$C_{1-10}$ alkyl,
(b) —$C_{3-12}$ cycloalkyl,
(c) —$(CH_2)_n$-phenyl,
(d) —$C_{2-10}$ alkenyl, or
(e) —$C_{2-10}$ alkynyl,
wherein said alkyl, alkenyl and alkynyl is optionally substituted with one or more
(i) halo,
(ii) —OH,
(iii) —CN,
(iv) —O—$C_{1-10}$ alkyl, or
(v) —$C_{3-12}$ cycloalkyl,
and said cycloalkyl and phenyl is optionally substituted with one or more
(i) halo,
(ii) —$C_{1-10}$ alkyl,
(iii) —OH,
(iv) —CN,
(v) —$C_{3-12}$ cycloalkyl, or
(vi) —O—$C_{1-10}$ alkyl;
$R^{10}$ is selected from the group consisting of
(1) —$C_{1-10}$ alkyl, or
(2) —$C_{3-12}$ cycloalkyl,
wherein said alkyl and cycloalkyl $R^{10}$ group is optionally substituted with one or more
(a) halo,
(b) —OH,
(c) —CN,
(d) —O—$C_{1-10}$ alkyl,
(e) —$C_{1-10}$ alkyl,
(f) —$C_{3-12}$ cycloalkyl,
(g) aryl selected from the group consisting of phenyl and napthyl, or
(h) heteroaryl;
$R^{11}$ is selected from the group consisting of
(1) hydrogen,
(2) —$C_{1-10}$ alkyl, and
(3) —$C_{3-12}$ cycloalkyl,
wherein said alkyl and cycloalkyl $R^{11}$ group is optionally substituted with one or more
(a) halo,
(b) —OH,
(c) —CN,
(d) —O—$C_{1-10}$ alkyl,
(e) —$C_{1-10}$ alkyl,
(f) —$C_{3-12}$ cycloalkyl,
(g) aryl selected from the group consisting of phenyl and napthyl, or
(h) heteroaryl;
$R^{12}$ is selected from the group consisting of
(1) hydrogen,
(2) —$C_{1-10}$ alkyl,
(3) —$C_{3-12}$ cycloalkyl,
wherein said alkyl and cycloalkyl $R^{12}$ groups are optionally substituted with one or more
(a) halo,
(b) —OH,
(c) —CN,
(d) —O—$C_{1-10}$ alkyl,
(e) —$C_{1-10}$ alkyl,
(f) —$C_{3-12}$ cycloalkyl,
(g) aryl selected from the group consisting of phenyl and napthyl, or
(h) heteroaryl;
$R^{13}$ is selected from the group consisting of
(1) C(=O)—$R^{16}$,
(2) C(=O)—NH—$R_{16}$, and
(3) $SO_2$—$R^{16}$,
wherein $R^{16}$ is selected from the group consisting of
(a) —$C_{1-10}$ alkyl,
(b) —$C_{3-12}$ cycloalkyl,
(c) —$(CH_2)_n$-phenyl,
(d) —$C_{2-10}$ alkenyl,
(e) —$C_{2-10}$ alkynyl, or
(f) heteroaryl,
wherein said alkyl, alkenyl and alkynyl $R^{16}$ moiety is optionally substituted with one or more
(i) halo,
(ii) —OH,
(iii) —CN,
(iv) —O—$C_{1-10}$ alkyl, or
(v) —$C_{3-12}$ cycloalkyl,
and said cycloalkyl, heteoraryl and phenyl $R^{16}$ moiety is optionally substituted with one or more
(i) halo,
(ii) —$C_{1-10}$ alkyl,
(iii) —OH,
(iv) —CN,
(v) —$C_{3-12}$ cycloalkyl,
(vi) —O—$C_{1-10}$ alkyl, or
(vii) heteoraryl;
$R^8$ is $C_{1-10}$ alkyl, wherein said alkyl is optionally substituted with one or more halogen;
$R^{9A}$, $R^{9B}$ and $R^{9C}$ are independently selected from the group consisting of
(1) hydrogen,
(2) halogen,
(3) —$C_{1-10}$ alkyl,
(4) —OH,
(5) —CN,
(6) —$C_{3-12}$ cycloalkyl, and
(7) —O—$C_{1-10}$ alkyl;
$R^{17}$ is selected from the group consisting of
(1) hydrogen, and
(2) chloro;
and pharmaceutically acceptable salts thereof, and individual enantiomers and diastereomers thereof.

In one embodiment, n is 1.

In another embodiment, $R^1$ is phenyl, optionally substituted with one or more halo. In certain embodiments, the $R^1$ phenyl group is unsubstituted.

In another embodiment, Q is

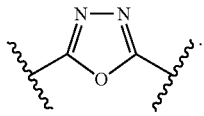

In another embodiment, Q is selected from the group consisting of (1) —CH$_2$—O—CH$_2$—,
(2) —CH$_2$—NH—CH$_2$—,
(3) —C(=O)—NH—CH$_2$—, and
(4) —CH$_2$—NH—C(=O)—.

In another embodiment, X is

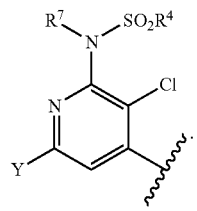

In alternative embodiments, X is selected from (1)

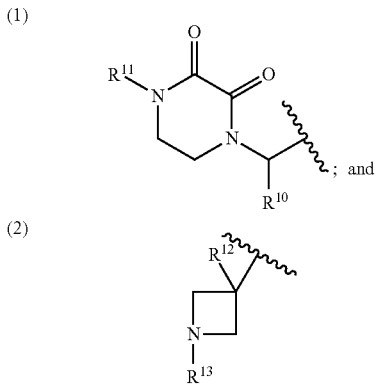

(2)

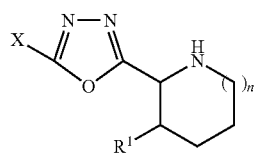

Exemplary Y groups for use in the invention include NR$^5$R$^6$, wherein R$^5$ and R$^6$ are selected from the group consisting of (1) hydrogen,
(2) —C$_{1-10}$ alkyl, and
(3) —C$_{1-10}$ alkyl-C$_{3-12}$ cycloalkyl, wherein said alkyl or cycloalkyl R$^5$ or R$^6$ group is optionally substituted with one or more (a) halo,
(b) —OH,
(c) —C$_{1-10}$ alkyl, or
(d) —O—C$_{1-10}$ alkyl.

In one embodiment, the compounds of formula (I) are compounds of formula (II)

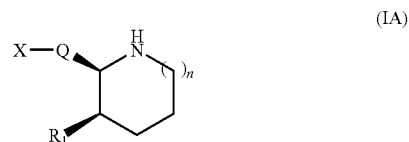

wherein R$^1$, X and n are as defined above, and pharmaceutically acceptable salts thereof, and individual enantiomers and diastereomers thereof.

In another embodiment, the compounds of formula (I) are compounds of formula (III)

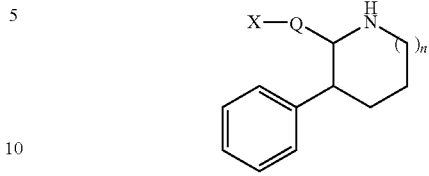

wherein X and n are as defined above, and pharmaceutically acceptable salts thereof, and individual enantiomers and diastereomers thereof.

Compounds of each of formulas (I)-(III) may be either in the cis or trans position, based on the position of the Q and R$^1$ substituents from the piperidine ring. In particular embodiments, each of formulas (I) to (III) are in the cis position, as shown below in formulas (IA), (IIA), and (IIIA):

(IA)

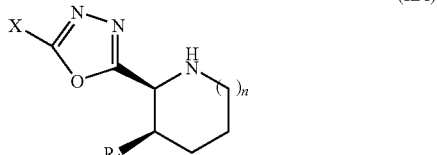

(IIA)

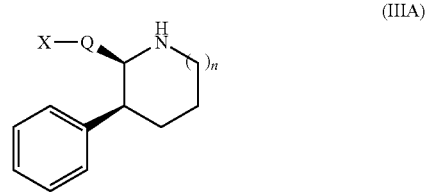

(IIIA)

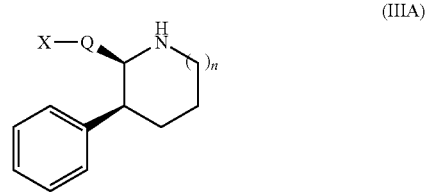

The invention is also directed to methods of treating mammals for diseases in which the β-secretase enzyme is involved, such as Alzheimer's disease, by administering a therapeutically effective amount of a compound of any of the embodiments of formula (I).

The invention is also directed to pharmaceutical compositions which include an effective amount of a compound of any of the embodiments of formula (I) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of any of the embodiments of formula (I) or a pharmaceutically acceptable salt thereof, with a pharmaceutical carrier or diluent.

In one embodiment, the invention is directed to methods of inhibiting BACE1 enzyme activity, by administering a therapeutically effective amount of a compound of any of the embodiments of formula (I).

In another embodiment, the invention is directed to methods of inhibiting BACE2 enzyme activity, by administering a therapeutically effective amount of a compound of any of the embodiments of formula (I).

The invention is also directed to a method for the manufacture of a medicament or a composition for treating Alzheimer's Disease in humans, comprising combining a compound of any of the embodiments of formula (I) or a pharmaceutically acceptable salt thereof, with a pharmaceutical carrier or diluent.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Suitable alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "$C_0$ alkyl," for example in the term "—$C_0$alkyl-$C_{6-12}$ aryl", refers to a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Suitable alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Suitable alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Suitable cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "heterocyclic," by itself or as part of another substituent, means a cycloalkyl group as defined above, in which one or more of the ring carbon atoms is replaced with a heteroatom (such as N or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolildinyl. In certain embodiments, heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. A suitable single ring aryl group for use in the invention is phenyl. Suitable fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Exemplary heteroaryl groups have from 5 to 12 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, thiadiazinyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of the invention have at least two asymmetric centers. Additional asymmetric centers may be present depending upon the nature of the various substituents on the molecule.

Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

Compounds described herein may contain one or more double bonds, and may thus give rise to cis/trans isomers as well as other configurational isomers. The present invention includes all such possible isomers as well as mixtures of such isomers.

Formulas (I)-(III) shown above without a definite stereochemistry at certain positions. The present invention includes all stereoisomers of formulas (I)-(III) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds claimed in this invention can be prepared according to the following general procedure methods.

Scheme 1A below outlines the preparation of protected cyclic amino acids of type 1A.1. Starting from pyridine 1A.1 esterification, triflate formation and Suzuki cross-coupling provides 1A.3. Subsequent saponification followed by reduction over Pt and Boc protection gives amine 1A.5. Starting from intermediates 1A.5, Scheme 1B outlines routes to either aminoalcohol intermediates of type 1B.1 or 1,3 diamines of type 1B.3.

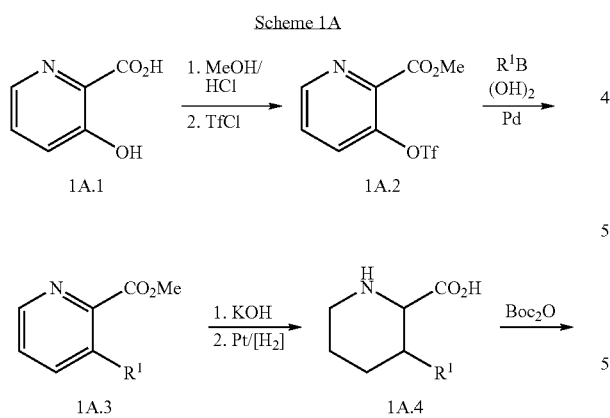

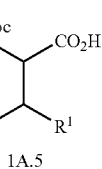

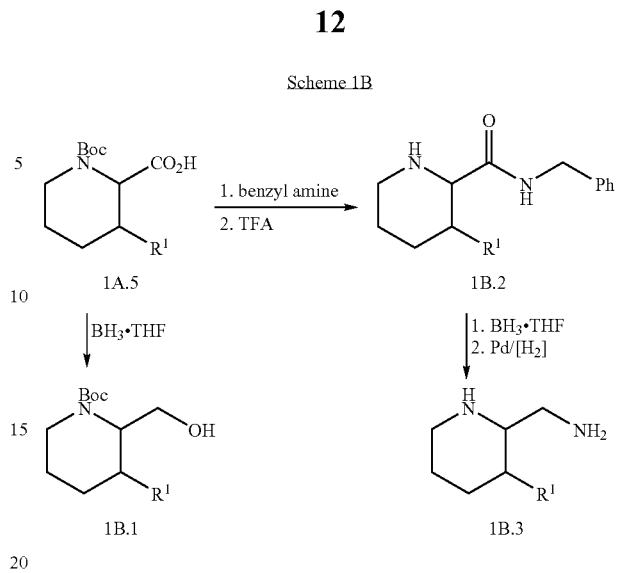

Scheme 1C below depicts the synthesis of carboxypyrrolidines of type 1C.3. Starting from acetylaminomalonitrile and reaction with various alpha,beta-unsaturated aldehydes gives ring-cyclized products of type 1C.1. Reduction followed by saponification, decarboxylation and Boc protection provides final Boc pyrrolidine 1C.3.

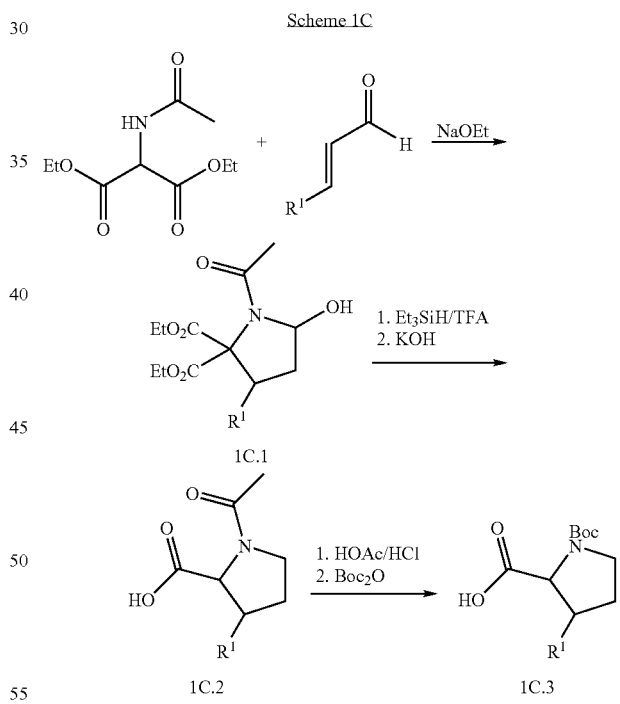

Scheme 2 outlines the synthesis of cyclopropylmethylamine derivatives ($NR^5R^6$) which are used in subsequent Schemes. Starting from cyclopropyl carboxylic acids of type 2.1, the benzyl amine 2.2 is generated via EDC coupling and borane reduction. Hydrogenation provides primary amine 2.3. Reductive methylation followed by hydrodenation leads to methyl amine 2.3. Further elaboration of 2.2 via amide coupling, borane reduction and hydrogenation of the benzyl group gives substituted amines of type 2.6 which are also used as coupling partners. Alternatively, reductive amination of 2.2 with various aldehydes followed by hydrogenation generates amines of type 2.7. Description of these intermediates can be found in WO 2005/065195.

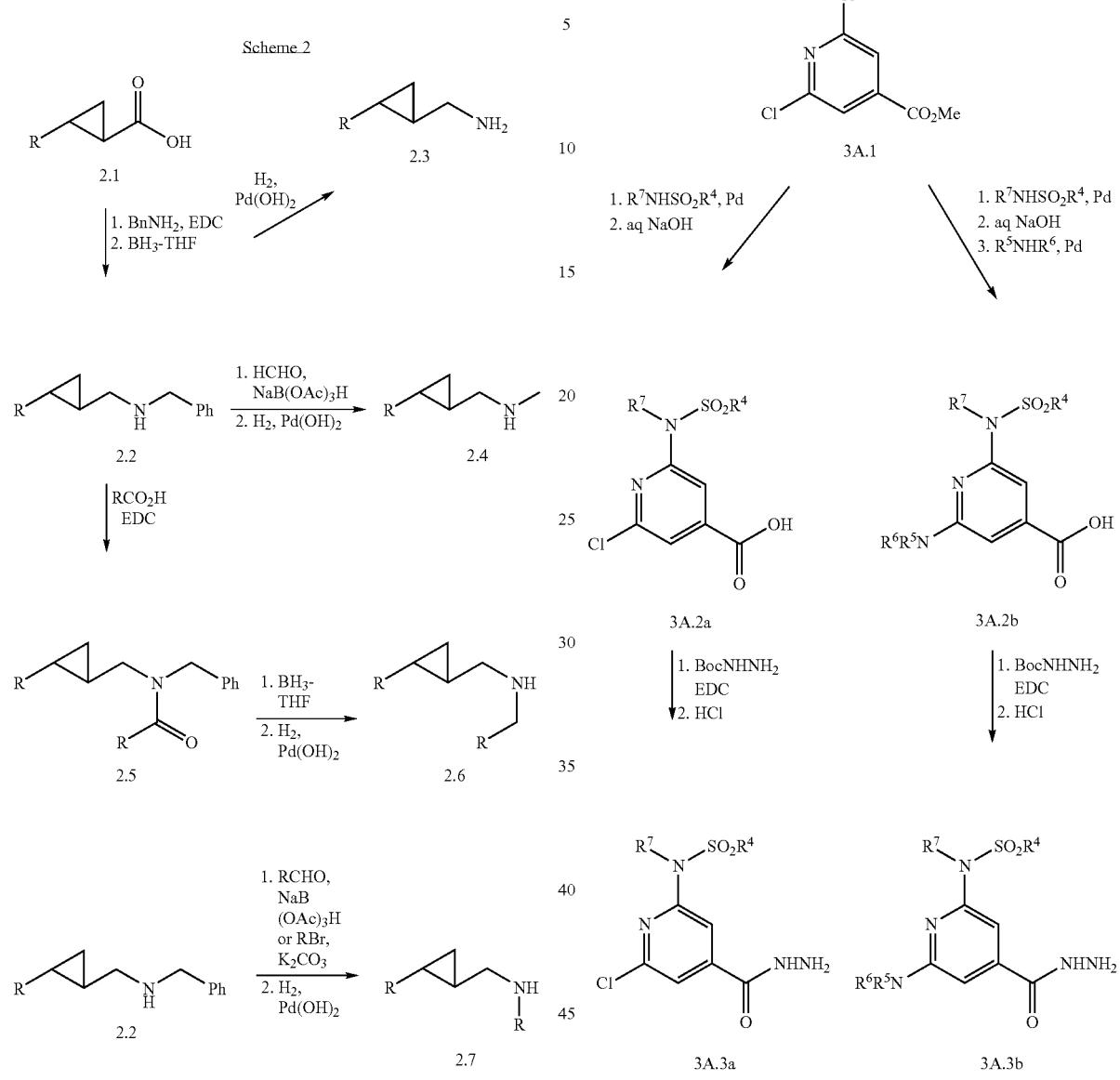

Scheme 3A describes the preparation of intermediates 3A.2a, 2b, 3a and 3b, to be used in the elaboration of various heterocycles, amides, esters or ether derivatives. 2,6-Dichloroiosonitinate methyl ester (3A.1) is first mono-substituted with an appropriate sulfonamide via Pd-catalyzed N-arylation and subsequently hydrolyzed to give the free acid 3A.2a which through coupling with protected hydrazide and deprotection gives the chloro intermediate 3A.3a. Alternatively, 3A.2a can first be subjected to Pd-catalyzed amination conditions to give 3A.2b and then elaborated to the hydrazine as before to give 3A.3b. Scheme 3B describes the syntheses of isophthalate precursors 3B.3a and 3B.3b which are useful intermediates towards elaborated examples. Starting from either 3-methoxy-methylisophthalate or 3-bromo-methyl-isophthalate a C—C or C—N bond formation can be performed followed by partial saponification of the diester, amide bond formation, and final installation of the acylazide to give the desired precursors.

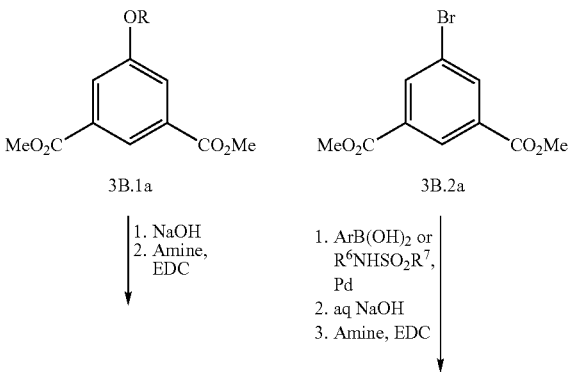

Scheme 3D outlines the synthesis of diketopiperazine (DKP) examples of type 3D.5. Alkylation of DKP 3D.1 followed by saponification gives acid 3D.2. Hydrazide formation, deprotection, acylation-dehydration and Boc removal gives final examples of type 3D.5.

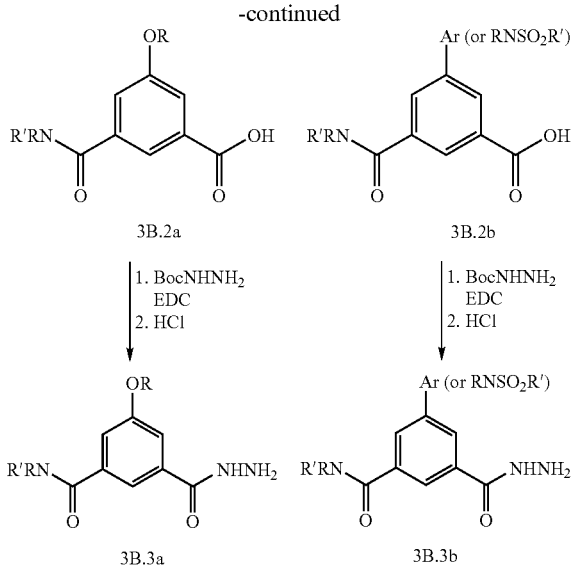

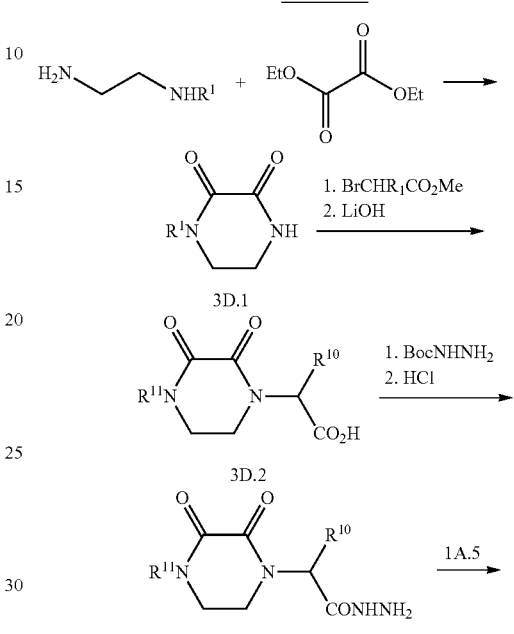

Scheme 3C describes the synthesis of azetidine examples of type 3C.4. 3-Carboxyazetidine is Cbz protected, coupled with Boc-hydrazide and the Boc group removed with HCl to give intermediate 3C.1. Coupling followed by dehydration, and deprotection gives azetidine 3C.3, which is then capped with the group "R" or coupled with various acids, acid chlorides, isocyanates, sulfonyl chlorides to give, upon final Boc removal, examples of type 3C.4.

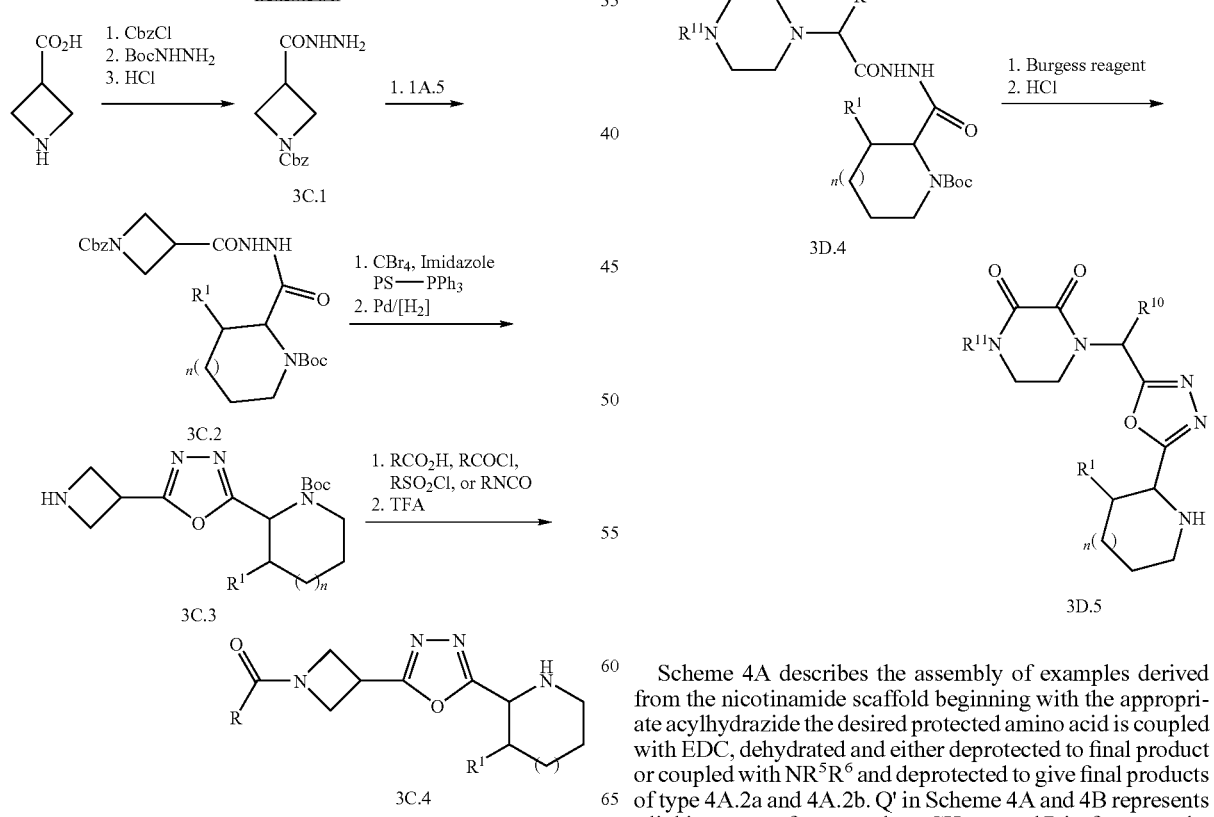

Scheme 4A describes the assembly of examples derived from the nicotinamide scaffold beginning with the appropriate acylhydrazide the desired protected amino acid is coupled with EDC, dehydrated and either deprotected to final product or coupled with $NR^5R^6$ and deprotected to give final products of type 4A.2a and 4A.2b. Q' in Scheme 4A and 4B represents a linking group, for example —$CH_2$—, and R is, for example, phenyl.

Scheme 4A
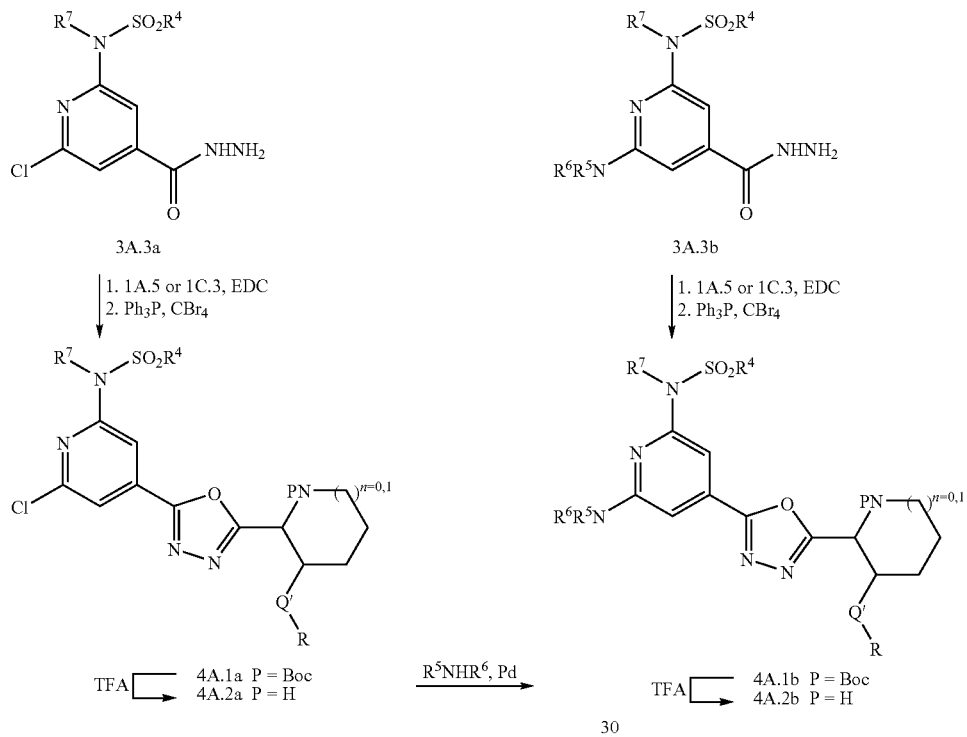
Scheme 4B describes assembly of examples of type 4B.2a and 4B.2b. Acylhydrazides 3B.3a and 3B.3b are first coupled with an appropriate acid of type 1A.5 or 1C.3, dehydrated an deprotected as before to give final structures of type 4B.2a and 4B.2b.
Scheme 4B
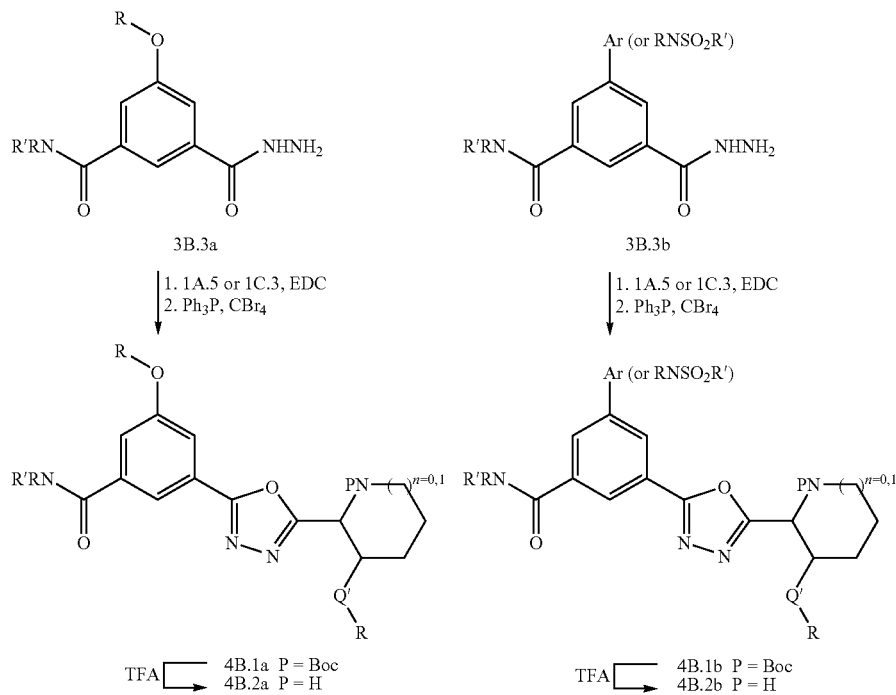

Scheme 5 describes the preparation of various combinations of ester, amide and ether linkages starting from acids of type 3.2b. Amide coupling using 1B.3 gives examples of type 5.5. Reduction to alcohol 5.1 followed by bromination and displacement with 1B.1 and deprotection, gives examples of type 5.7. Preparation of chloride 5.2 from 5.1, followed by displacement with 1A.5 and deprotection gives esters of type 5.8. Azide displacement of 5.2, followed by reduction to the amine 5.3 and amide bond formation with 1A.5 gives after deprotection examples of type 5.4.

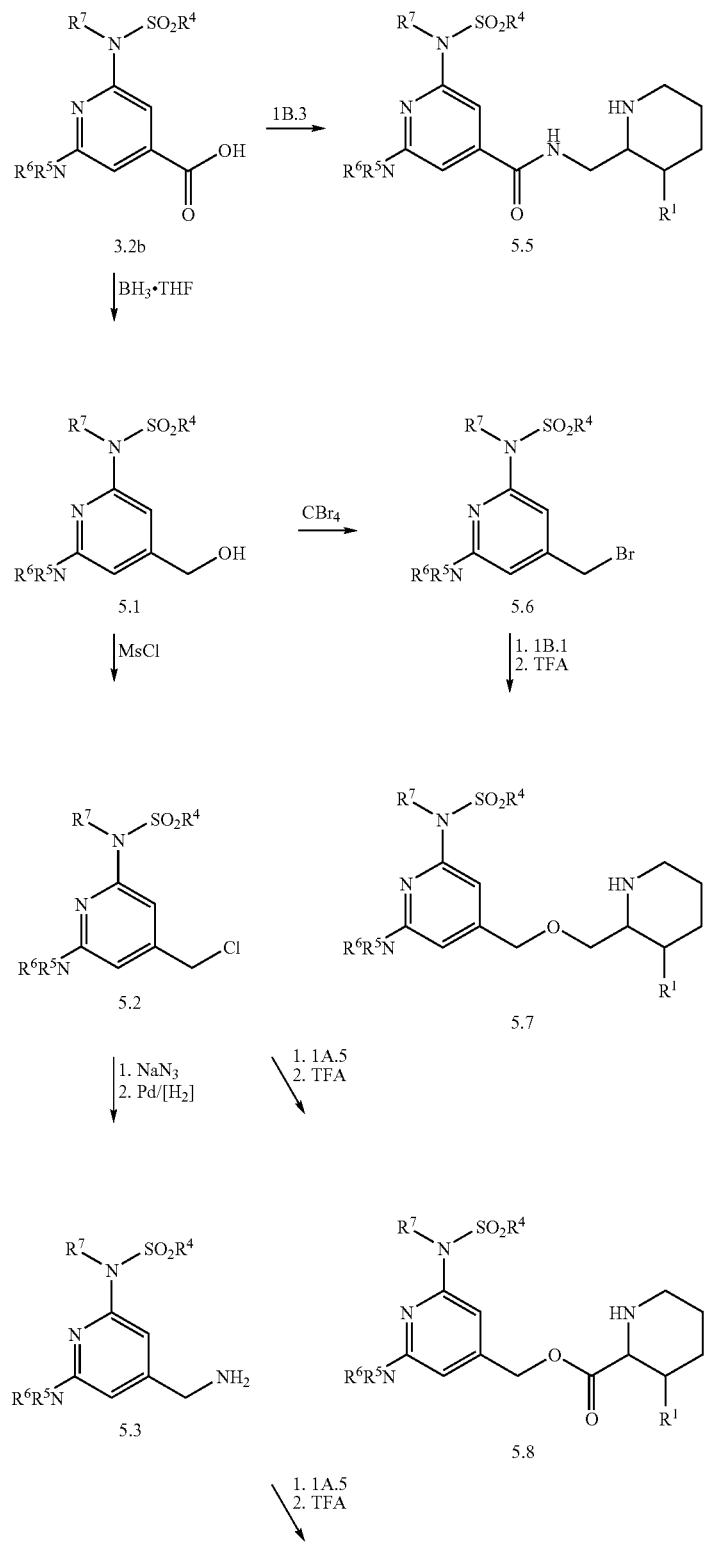

Scheme 5

-continued

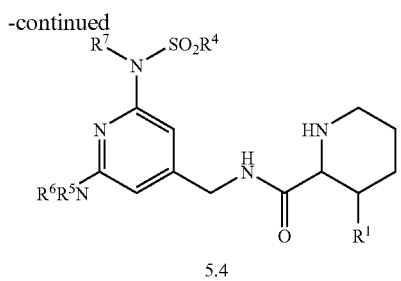

5.4

The term "substantially pure" means that the isolated material is at least 90% pure, as assayed by analytical techniques known in the art. In one embodiment, the isolated material is at least 95% pure. In another embodiment, the isolated material is at least 99% pure The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particular salts are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular salts are the citric, hydrobromic, hydrochloric, trifluoroacetic, maleic, phosphoric, sulfuric, fumaric, and tartaric acids.

The present invention is directed to the use of the compounds of formulas (I) to (III) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

Examples of combinations of the compounds of the present invention with other drugs in either unit dose or kit form include combinations with anti-Alzheimer's agents, for example other beta-secretase inhibitors or gamma-secretase inhibitors; glycine transport inhibitors, tau phosphorylation inhibitors; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α5 receptor ligands; $GABA_B$ receptor ligands; potassium channel blockers; neuronal nicotinic agonists; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. In certain embodiments, each tablet contains from about 0.1 mg to about 500 mg of the active ingredient and each cachet or capsule contains from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight. For example, the compounds may be given as a single daily dose or in divided doses two to six times a day, or in sustained release form. The total daily dosage is from about 1.0 mg to about 2000 mg (for example, from about 0.1 mg to about 20 mg per kg of body weight). In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, for example once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is performed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 μM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 200 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediates

Intermediate 1A.5: 1-(tert-butoxycarbonyl)-3-phenylpiperidine-2-carboxylic acid

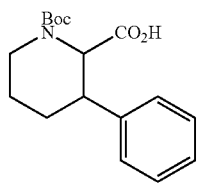

Step A: Esterification (Scheme 1A)

To a solution of 3-hydroxypyridine-2-carboxylic acid (100 g, 719 mmol) in anhydrous methanol (300 ml) was added dry HCl gas until the saturation point of the solution was achieved. The reaction was heated to reflux for 15 h and then cooled and degassed with argon. The solution was concentrated in vacuo to give a white solid which was dissolved in water (250 ml). The pH of the solution was adjusted to ~7.5 with the slow addition of solid sodium bicarbonate. The resulting suspension was extracted with EtOAc (2×300 ml), and the organic portion was dried over magnesium sulfate, filtered, and concentrated in vacuo to yield methyl 3-hydroxypyridine-2-carboxylate as an oily residue which crystallized on standing (99.2 g).

Step B: Triflate Preparation

To a solution of methyl 3-hydroxypyridine-2-carboxylate (80 g, 523 mmol) in anhydrous dichloromethane (250 ml) was added triethylamine (58.2 g, 575 mmol). The solution was cooled to 0° C., and trifluoromethanesulfonyl chloride (97 g, 575 mmol) was added dropwise. The reaction suspension was allowed to stir at 0° C. for 1 h, and it was then warmed to rt to stir for 4 h. The solid triethylammonium chloride was removed via filtration, and the filtrate was concentrated in vacuo to yield methyl 3-{[(trifluoromethyl)sulfonyl]oxy}pyridine-2-carboxylate as an oily residue (148.6 g).

Step C: Suzuki Reaction

To a solution of methyl 3-{[(trifluoromethyl)sulfonyl]oxy}pyridine-2-carboxylate (148.6 g, 521 mmol) in anhydrous toluene (550 ml) were added potassium carbonate (148.6 g), tetrakis(triphenylphosphine)palladium(0) (6 g), and phenyl boronic acid (70 g, 574 mmol). The reaction was equipped with a mechanical stirring apparatus and heated to reflux for 2 h. The reaction suspension was filtered through a bed of celite and washed with EtOAc. The filtrate was concentrated in vacuo and purified via flash chromatography (silica, 20% EtOAc/hexanes isocratic) to provide methyl 3-phenylpyridine-2-carboxylate (88.5 g).

Step D: Ester Saponification

To a solution of methyl 3-phenylpyridine-2-carboxylate (61.0 g, 286 mmol) in absolute ethanol was added potassium hydroxide (32.0 g, 572 mmol). After stirring at 50° C. for 2 h, the reaction mixture was cooled and adjusted to pH ~7.5 with 1M phosphoric acid. The mixture was diluted with water (1 L) and extracted with EtOAc (2×600 ml). The organic portion was dried over magnesium sulfate, filtered, and concentrated in vacuo to yield 3-phenylpyridine-2-carboxylic acid as a solid (54.7 g).

Step E: Pyridine Reduction and Boc Protection

To a suspension of platinum oxide hydrate (1 g) in methanol (10 ml) was added a solution of 3-phenylpyridine-2-carboxylic acid (10.5 g, 52.8 mmol) in methanol (20 ml). The reaction was charged with 1 atm hydrogen gas and allowed to stir for 36 h. The reaction suspension was filtered and concentrated in vacuo to yield a solid residue which was dissolved in water (20 ml). To the solution were added acetone (20 ml) and sodium bicarbonate (13.3 g, 158 mmol), followed by di-tert-butyldicarbonate (12.7 g, 58 mmol) with vigorous stirring. The resulting reaction suspension was allowed to stir for 12 h, at which point the pH was adjusted to 5.5 using 1M phosphoric acid. The product was extracted with EtOAc (2×50 ml), and the organics were dried over magnesium sulfate, filtered, and concentrated in vacuo to yield 1-(tert-butoxycarbonyl)-3-phenylpiperidine-2-carboxylic acid as an oily residue which crystallized on standing (8.2 g). LCMS (M+H)=306.1.

Intermediate 1B.1: tert-butyl 2-(hydroxymethyl)-3-phenylpiperidine-1-carboxylate (Scheme 1B)

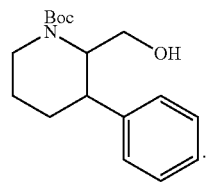

To a solution of 1-(tert-butoxycarbonyl)-3-phenylpiperidine-2-carboxylic acid (416 mg, 1.36 mmol) in THF (2 ml) at 0° C. was added 1M borane-THF complex in THF (4.1 ml, 3.01 mmol). The reaction was warmed to rt and allowed to stir for 18 h. The reaction was cooled to 0° C., quenched with the careful addition of methanol, and concentrated in vacuo to yield tert-butyl 2-(hydroxymethyl)-3-phenylpiperidine-1-carboxylate (82%). HRMS (ES, M+Na) calcd for $C_{17}H_{25}NO_3$: 314.1726, found: 314.1720. $^1$H NMR (400 MHz, $CD_3OD$) δ 7.34-7.13 (m, 5H), 4.46 (m, 1H), 4.06 (d, J=13.0 Hz, 1H), 3.75 (m, 1H), 3.09 (m, 1.5H), 2.99 (m, 1.5H), 2.06 (m, 1H), 1.82 (m, 2H), 1.59 (m, 1H), 1.48 (s, 9H).

Intermediate 1B.3: 2-(ammoniomethyl)-3-phenylpiperidinium dichloride

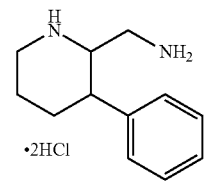

Step A: Amide Coupling (Scheme 1B)

To a solution of 1-(tert-butoxycarbonyl)-3-phenylpiperidine-2-carboxylic acid (1.03 g, 3.36 mmol) in DMF (5 ml) were added benzyl amine (0.4 ml, 3.70 mmol), 1-hydroxybenzotriazole (567 mg, 3.70 mmol), and 1-(3-dimethylaminopropyl)-3-ethylcarbodiimide hydrochloride (949 mg, 4.70 mmol). The reaction was adjusted to pH 7 with the addition of diisopropylethylamine and allowed to stir for 1 h. The reaction mixture was diluted with EtOAc, washed with saturated sodium bicarbonate (3×) and brine (2×), dried over sodium sulfate, filtered, and concentrated in vacuo to yield tert-butyl 2-[(benzylamino)carbonyl]-3-phenylpiperidine-1-carboxylate (100%).

Step B: Boc Deprotection

A solution of tert-butyl 2-[(benzylamino)carbonyl]-3-phenylpiperidine-1-carboxylate (1.44 g, 3.65 mmol) in 1:1 TFA/dichloromethane (10 ml) was allowed to stir for 3 h. The reaction was concentrated in vacuo, and the residue was dissolved in acetonitrile/water and lyophilized to yield 2-[(benzylamino)carbonyl]-3-phenylpiperidinium trifluoroacetate (91%).

Step C: Amide Reduction

To a solution of 2-[(benzylamino)carbonyl]-3-phenylpiperidinium trifluoroacetate (604 mg, 1.48 mmol) in THF (2 ml) at 0° C. was added 2M borane-THF complex in THF (7.5 ml, 14.8 mmol). The reaction was allowed to stir for 18 h. Additional 2M borane-THF complex in THF (1.5 ml, 2.96 mmol) was added to the reaction mixture and allowed to stir for an additional 24 h. The reaction was quenched with methanol, concentrated in vacuo, and concentrated again from 4M HCl in dioxane. The crude product was purified via reverse phase preparative HPLC to yield 1-phenyl-N-[(3-phenylpiperidin-2-yl)methyl]methanamine (20%). $^1$H NMR (400 MHz, CD$_3$OD) δ 7.42-7.28 (m, 10H), 4.05 (m, 2H), 3.82 (m, 1H), 3.58 (d, J=10.9 Hz, 0.4H), 3.38 (m, 2H), 3.21 (m, 0.6H), 2.96 (m, 1H), 2.20 (m, 1H), 1.97 (m, 3H).

Step D: Benzyl Deprotection

To a solution of 1-phenyl-N-[(3-phenylpiperidin-2-yl)methyl]methanamine (101 mg, 0.359 mmol) in methanol (5 ml) were added 4M HCl in dioxane (0.090 ml, 0.359 mmol) and palladium hydroxide (28.9 mg, 0.036 mmol). The reaction mixture was charged with 1 atm hydrogen gas and allowed to stir for 18 h. The reaction mixture was filtered through celite, and to the filtrate was added 4M HCl in dioxane (0.090 ml, 0.359 mmol). The reaction was allowed to stir for 1 h and concentrated in vacuo to yield 2-(ammoniomethyl)-3-phenylpiperidinium dichloride (61%). LCMS (M+H)=191.0.

Intermediate 1C.3:
1-(tert-butoxycarbonyl)-3-phenylproline

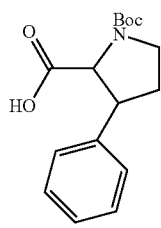

Step A Cyclization (Scheme 1C):

To a solution of diethyl acetamidomalonate (75.0 g, 345 mmol) in ethanol (375 ml) at 0° C. was added sodium metal (6.9 g, 36 mmol). Cinnamaldehyde (50.0 g, 378 mmol) was added dropwise to the resulting solution. The reaction was warmed to rt and allowed to stir for 2 h. Acetic acid (7 ml) was added, and the solution was concentrated. The residue was dissolved in EtOAc, washed with water and brine, dried over sodium sulfate, filtered, and concentrated in vacuo. The crude solid was triturated with hexanes/EtOAc to yield diethyl 1-acetyl-5-hydroxy-3-phenylpyrrolidine-2,2-dicarboxylate as a white solid (96%).

Step B:

To a solution of diethyl 1-acetyl-5-hydroxy-3-phenylpyrrolidine-2,2-dicarboxylate (116.0 g, 331 mmol) and triethylsilane (80 ml, 497 mmol) in dichloromethane (675 ml) was added trifluoroacetic acid (254 ml, 3.32 mol) dropwise with stirring over 45 min. The reaction was allowed to stir for 2.5 h at rt and was then concentrated and redissolved in EtOAc. The organics were washed with sat'd sodium bicarbonate, dried over sodium sulfate, filtered, and concentrated in vacuo to yield diethyl 1-acetyl-3-phenylpyrrolidine-2,2-dicarboxylate as an oil (100%).

Step C:

To a solution of diethyl 1-acetyl-3-phenylpyrrolidine-2,2-dicarboxylate (110.6 g, 331 mmol) in ethanol (500 ml) was added potassium hydroxide (55.7 g, 993 mmol). The reaction was allowed to stir at reflux for 8 h and was then concentrated. The residue was dissolved in water and extracted with EtOAc. The aqueous layer was cooled to 0° C., carefully acidified to pH 2-3 using conc HCl, and exhaustively extracted with EtOAc. The combined organics were dried over sodium sulfate, filtered, and concentrated in vacuo to yield 1-acetyl-3-phenylproline as a solid (95%).

Step D:

To a solution of 1-acetyl-3-phenylproline (73.0 g, 313 mmol) in acetic acid (125 ml) was added 8N HCl (375 ml). The reaction was allowed to stir at reflux for 8 h and was then concentrated in vacuo. The residue was dissolved in 1N NaOH (800 ml) and THF (800 ml), and to this solution was added di-tert-butyl dicarbonate (89.0 g, 407 mmol). The reaction was allowed to stir for 20 h at room temperature. The reaction was diluted with EtOAc, and the layers were separated. The aqueous layer was carefully acidified using 2N HCl and exhaustively extracted with EtOAc. The combined organics were dried over sodium sulfate, filtered, and concentrated in vacuo to yield 1C.3 or 1-(tert-butoxycarbonyl)-3-phenylproline (56%). LCMS (M+H)=292.1 (M-100, major ion).

Intermediates 3A. 3a: 2N-[6-chloro-4-(hydrazinocarbonyl)pyridin-2-yl]-N-methylmethanesulfonamide (Scheme 3A)

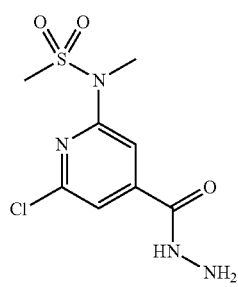

Prepared from Intermediate 4.2a.1 page 40 of WO2006/057945 using conditions similar to that described in the preparation of Intermediate 4.3c.1 page 51 of WO2006/057945 involving Boc-hydrazine coupling with EDC/HOAt followed by subsequent Boc deprotection using HCl(g) to give after concentration final intermediate as HCl salt. LCMS (M+H)=279.1.

Intermediate 3A.3b: N-(4-(hydrazinocarbonyl)-6-{methyl[(trans-2-methylcyclopropyl)methyl]amino}pyridin-2-yl)-N-methylmethanesulfonamide

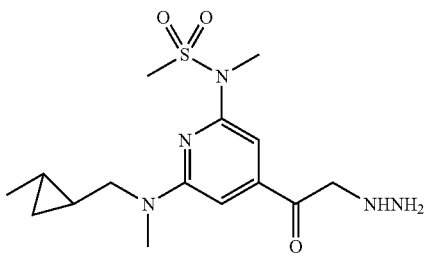

Prepared from Intermediate 4.2c.3 from page 43 of WO 2006/057945 is a manner similar to that described above in Intermediate 3A.3a involving involving Boc-hydrazine coupling with EDC/HOAt followed by subsequent Boc deprotection using HCl(g) to give after concentration final intermediate as HCl salt. LCMS (M+H)=342.1.

Intermediate 3C.3: tert-butyl 2-(5-azetidin-3-yl-1,3,4-oxadiazol-2-yl)-3-phenylpiperidine-1-carboxylate

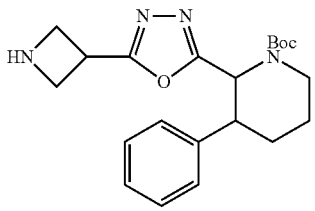

Step A: Cbz Protection

To a solution of azetidine-3-carboxylic acid (5.00 g, 49.5 mmol) in dioxane (325 ml) were added 1N sodium hydroxide (124 ml, 124 mmol) and benzyl chloroformate (8.44 ml, 59.3 mmol). The reaction was allowed to stir for 18 h. The reaction was diluted with 3N HCl until pH 2 was obtained. The product was extracted with EtOAc (2×), washed with brine, dried over sodium sulfate, filtered, and concentrated in vacuo. The crude material was purified via flash chromatography (silica, 0-70% methanol (0.5% acetic acid)/dichloromethane) to yield 1-[(benzyloxy)carbonyl]azetidine-3-carboxylic acid as a yellow oil (73%). $^1$H NMR (400 MHz, CD$_3$OD) δ 7.37-7.26 (m, 5H), 5.08 (s, 2H), 4.18 (m, 2H), 4.11 (br s, 2H), 3.44 (m, 1H).

Step B: Amide Coupling and Boc Deprotection

To a solution of 1-[(benzyloxy)carbonyl]azetidine-3-carboxylic acid (6.00 g, 25.5 mmol) in DMF (150 ml) were added tert-butyl carbazate (4.05 g, 30.6 mmol), 1-(3-dimethylaminopropyl)-3-ethylcarbodiimide hydrochloride (7.34 g, 38.3 mmol), 1-hydroxy-7-azabenzotriazole (3.47 g, 25.5 mmol), and diisopropylethylamine (6.66 ml, 38.3 mmol). The reaction was allowed to stir for 1 h. The product was extracted with EtOAc, washed with 3M lithium chloride (3×), dilute HCl, and brine, dried over sodium sulfate, filtered, and concentrated in vacuo. The crude material was purified via flash chromatography (silica, 60% EtOAc/hexanes isocratic) to afford the Boc protected product as a white foam. A solution of the protected material in EtOAc was cooled to 0° C., saturated with HCl gas, and allowed to stir for 8 h. The reaction was concentrated in vacuo, and the residue was dissolved in EtOAc, washed with 1N sodium hydroxide, dried over sodium sulfate, filtered, and concentrated in vacuo to yield benzyl 3-(hydrazinocarbonyl)azetidine-1-carboxylate (75%).

Step C: Amide Coupling

To a solution of benzyl 3-(hydrazinocarbonyl)azetidine-1-carboxylate (350 mg, 1.40 mmol) in DMF (10 ml) were added 1-(tert-butoxycarbonyl)-3-phenylpiperidine-2-carboxylic acid (1A.5, 427 mg, 1.40 mmol), 1-(3-dimethylaminopropyl)-3-ethylcarbodiimide hydrochloride (322 mg, 1.68 mmol), and 1-hydroxy-7-azabenzotriazole (95.3 mg, 0.700 mmol). The reaction was allowed to stir for 48 h, and then poured onto 10% potassium hydrogen sulfate and diluted with water (10 ml) and EtOAc (30 ml). The organic portion was isolated, washed with 3M lithium chloride (2×) and brine, dried over sodium sulfate, filtered, and concentrated in vacuo. The crude material was purified via flash chromatography (silica, 0-50% EtOAc/hexanes) to yield tert-butyl 2-{[2-({1-[(benzyloxy)carbonyl]azetidin-3-yl}carbonyl)hydrazino]carbonyl}-3-phenylpiperidine-1-carboxylate (31%).

Step D: Cyclodehydration

To a solution of tert-butyl 2-{[2-({1-[(benzyloxy)carbonyl]azetidin-3-yl}carbonyl)hydrazino]carbonyl}-3-phenylpiperidine-1-carboxylate (235 mg, 0.44 mmol) in dichloromethane (4 ml) at 0° C. were added imidazole (71.6 mg, 1.05 mmol), polystyrene bound triphenyl phosphine (471 mg, 0.96 mmol, 2.04 g/mmol), and carbon tetrabromide (320 mg, 0.96 mmol). The reaction was warmed to rt and allowed to stir for 18 h. The reaction mixture was filtered and rinsed with dichloromethane. The filtrate was concentrated to give an oil. The crude material was purified via flash chromatography (silica, 0-35% EtOAc/hexanes) to yield tert-butyl 2-(5-{1-[(benzyloxy)carbonyl]azetidin-3-yl}-1,3,4-oxadiazol-2-yl)-3-phenylpiperidine-1-carboxylate (96%) as a colorless oil.

Step E: Cbz Removal

To a solution of tert-butyl 2-(5-{1-[(benzyloxy)carbonyl]azetidin-3-yl}-1,3,4-oxadiazol-2-yl)-3-phenylpiperidine-1-carboxylate (200 mg, 0.39 mmol) in ethanol (10 ml) was added 10% palladium on carbon (20.0 mg). The reaction was charged with 1 atm hydrogen gas and allowed to stir for 1 h. The reaction was filtered through celite, and the filtrate was concentrated to yield tert-butyl 2-(5-azetidin-3-yl-1,3,4-oxadiazol-2-yl)-3-phenylpiperidine-1-carboxylate (100%). LCMS (M+H)=385.2.

Example 1

(cis-2S,3S and cis-2R,3R)-2-[5-(1-pentanoylazetidin-3-yl)-1,3,4-oxadiazol-2-yl]-3-phenylpiperidine
(Scheme 3C)

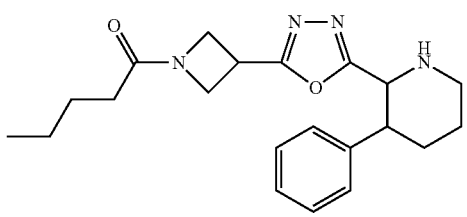

To a solution of tert-butyl cis-2-(5-azetidin-3-yl-1,3,4-oxadiazol-2-yl)-3-phenylpiperidine-1-carboxylate (3C.3, 20.0 mg, 0.05 mmol) in dichloromethane (1 ml) was added valeryl chloride (0.007 ml, 0.06 mmol) and triethylamine (0.007 ml, 0.05 mmol). The reaction was allowed to stir for 0.5 h. TFA (0.3 ml) was added to the reaction and allowed to stir for an additional 1 h. The reaction was concentrated and purified via reverse phase preparative HPLC. Product containing fractions were treated with aqueous sodium bicarbonate. The product was extracted with EtOAc, washed with brine, dried over sodium sulfate, filtered, and concentrated to yield cis-2-[5-(1-pentanoylazetidin-3-yl)-1,3,4-oxadiazol-2-yl]-3-phenylpiperidine (52%). $^1$H NMR (400 MHz, CD$_3$OD) δ 7.22-7.08 (m, 5H), 4.59 (d, J=5.2 Hz, 1H), 4.47 (dt, J=4.4 Hz, 1H), 4.23 (q, J=9.3 Hz, 1H), 4.11 (dd, J=9.0, 5.8 Hz, 0.5H), 4.05 (dd, J=8.4, 5.6 Hz, 0.5H), 3.95 (m, 1H), 3.84 (m, 1H), 3.33 (m, 2H), 2.89 (m, 1H), 2.34 (m, 1H), 2.10 (m, 2H), 1.92 (m, 2H), 1.74 (m, 1H), 1.54 (quint, J=7.5 Hz, 2H), 1.35 (m, 2H), 0.93 (dt, J=7.4, 2.9 Hz, 3H).

The following azetidine examples in Table 1 were prepared in a manner similar to Example 1 or through the use of the requisite carboxylic acid in conjunction with an appropriate coupling agent such as EDC in the presence of HOAt:

TABLE 1

Azetidine Examples

| EX | Structure | Parent MW | MS M + 4 | Stereochemistry | IUPAC Name |
|---|---|---|---|---|---|
| 2 | 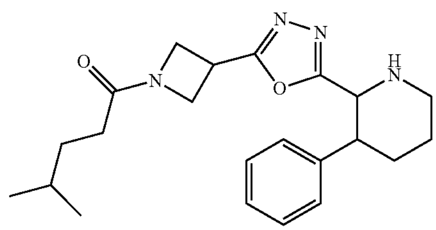 | 382.51 | 383 | CIS, MIXT. OF RR AND SS | cis-2-{5-[1-(4-methylpentanoyl)azetidin-3-yl]-1,3,4-oxadiazol-2-yl}-3-phenylpiperidine |
| 3 | 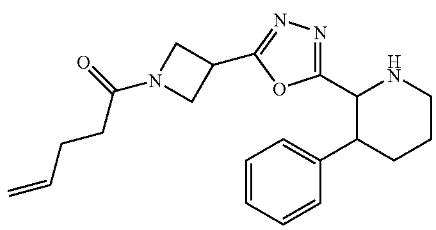 | 366.47 | 367 | CIS, MIXT. OF RR AND SS | cis-2-[5-(1-pent-4-enoylazetidin-3-yl)-1,3,4-oxadiazol-2-yl]-3-phenylpiperidine |
| 4 | 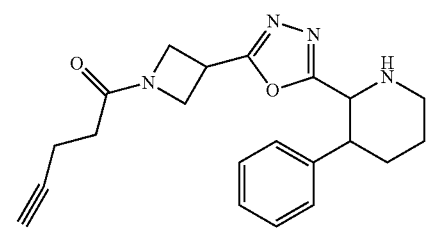 | 364.45 | 365 | CIS, MIXT. OF RR AND SS | cis-2-[5-(1-pent-4-ynoylazetidin-3-yl)-1,3,4-oxadiazol-2-yl]-3-phenylpiperidine |
| 5 | 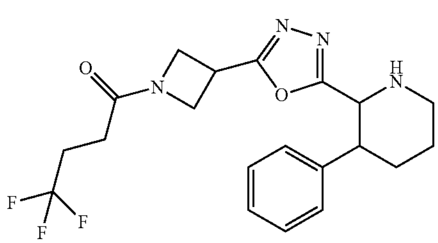 | 408.43 | 409 | CIS, MIXT. OF RR AND SS | cis-3-phenyl-2-{5-[1-(4,4,4-trifluorobutanoyl)azetidin-3-yl]-1,3,4-oxadiazol-2-yl}piperidine |
| 6 | 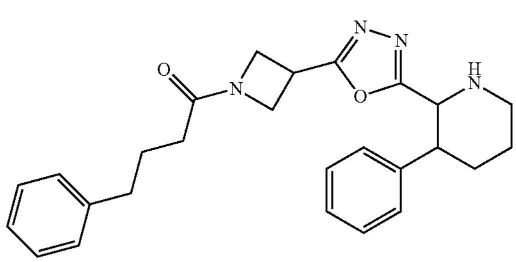 | 430.56 | 431 | CIS, MIXT. OF RR AND SS | cis-3-phenyl-2-{5-[1-(4-phenylbutanoyl)azetidin-3-yl]-1,3,4-oxadiazol-2-yl}piperidine |

TABLE 1-continued

Azetidine Examples

| EX | Structure | Parent MW | MS M + 4 | Stereochemistry | IUPAC Name |
| --- | --- | --- | --- | --- | --- |
| 7 | 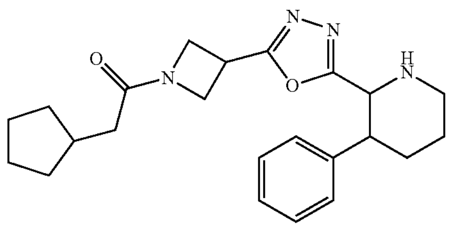 | 394.52 | 395 | CIS, MIXT. OF RR AND SS | cis-2-{5-[1-(cyclopentylacetyl)azetidin-3-yl]-1,3,4-oxadiazol-2-yl}-3-phenylpiperidine |
| 8 | 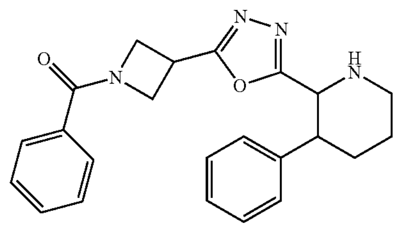 | 388.47 | 389 | CIS, MIXT. OF RR AND SS | cis-2-[5-(1-benzoylazetidin-3-yl)-1,3,4-oxadiazol-2-yl]-3-phenylpiperidine |
| 9 | 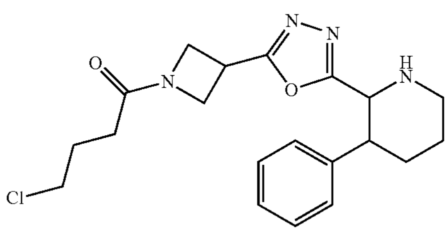 | 388.90 | 389 | CIS, MIXT. OF RR AND SS | cis-2-{5-[1-(4-chlorobutanoyl)azetidin-3-yl]-1,3,4-oxadiazol-2-yl}-3-phenylpiperidine |
| 10 | 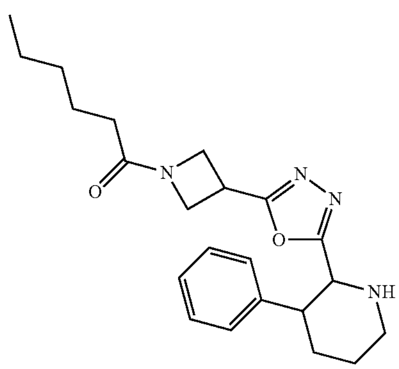 | 382.5 | 383 | CIS, MIXT. OF RR AND SS | cis-2-[5-(1-hexanoylazetidin-3-yl)-1,3,4-oxadiazol-2-yl]-3-phenylpiperidine |
| 11 | 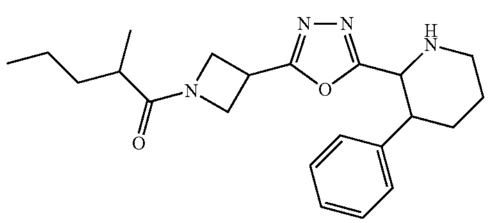 | 382.5 | 383 | RACEMIC AND CIS, MIXT. OF RR AND SS (4 possible stereoisomers) | cis-2-{5-[1-(2-methylpentanoyl)azetidin-3-yl]-1,3,4-oxadiazol-2-yl}-3-phenylpiperidine |
| 12 | 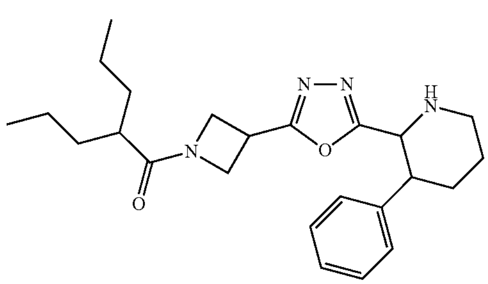 | 410.5 | 411 | CIS, MIXT. OF RR AND SS | cis-3-phenyl-2-{5-[1-(2-propylpentanoyl)azetidin-3-yl]-1,3,4-oxadiazol-2-yl}piperidine |

TABLE 1-continued

Azetidine Examples

| EX | Structure | Parent MW | MS M+4 | Stereochemistry | IUPAC Name |
|---|---|---|---|---|---|
| 13 | 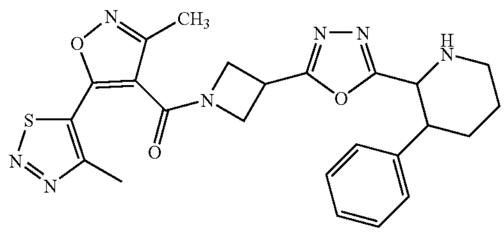 | 491.5 | 492 | CIS, MIXT. OF RR AND SS | cis-2-[5-(1-{[3-methyl-5-(4-methyl-1,2,3-thiadiazol-5-yl)isoxazol-4-yl]carbonyl}azetidin-3-yl)-1,3,4-oxadiazol-2-yl]-3-phenylpiperidine |
| 14 | 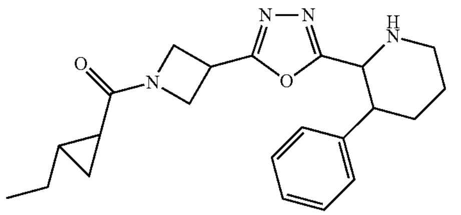 | 380.4 | 381 | TRANS (RR, SS) CIS, MIXT. OF RR AND SS (4 possible stereoisomers) | cis-2-(5-{1-[(trans-2-ethylcyclopropyl)carbonyl]azetidin-3-yl}-1,3,4-oxadiazol-2-yl)-3-phenylpiperidine |

Example 15

1-butyl-4-(phenyl[5-(cis-3-phenylpiperidin-2-yl)-1,3,4-oxadiazol-2-yl]methyl)piperazine-2,3-dione
(Scheme 3D)

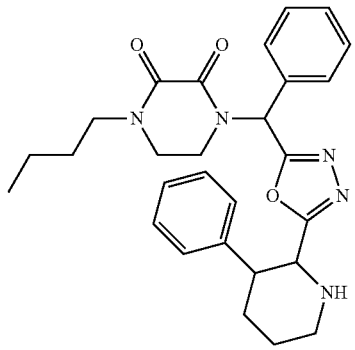

Step A: Diketopiperazine Formation

To a solution of N-butylethylenediamine (4.78 ml, 34.4 mmol) in isopropanol (60 ml) at 0° C. under a nitrogen atmosphere was added diethyloxalate (4.67 ml, 34.4 mmol). The reaction was allowed to warm to rt and heated to reflux for 6 h. The reaction was concentrated in vacuo and purified via flash chromatography (silica) to yield 1-butylpiperazine-2,3-dione (44%).

Step B: Installation of Phenylacetate Moiety

To a solution of 1-butylpiperazine-2,3-dione (1.6 g, 9.1 mmol) in DMF (12 ml) at 0° C. was added sodium hydride (0.25 g, 10.4 mmol). After stirring for 20 min, methyl α-bromophenylacetate (1.6 ml, 10.0 mmol) was added to the reaction. The reaction was warmed to rt and allowed to stir for 18 h. The reaction was quenched with water, diluted with EtOAc, washed with 3M LiCl, water, and brine, dried over sodium sulfate, filtered, and concentrated in vacuo. The crude product was purified via flash chromatography (silica) to yield methyl (4-butyl-2,3-dioxopiperazin-1-yl)(phenyl)acetate (86%).

Step C: Saponification

To a solution of methyl (4-butyl-2,3-dioxopiperazin-1-yl)(phenyl)acetate (2.5 g, 9.1 mmol) in 1:1 methanol/THF (40 ml) was added 1N LiOH (18.2 ml, 18.2 mmol). The reaction was warmed to rt and allowed to stir for 18 h. The reaction mixture was cooled to 0° C., adjusted to pH 2 with conc HCl, and concentrated in vacuo. The residue was dissolved in EtOAc, washed with brine, dried over sodium sulfate, filtered, and concentrated to yield (4-butyl-2,3-dioxopiperazin-1-yl)(phenyl)acetic acid (100%).

Step D: Amide Coupling and Boc Deprotection

To a solution of (4-butyl-2,3-dioxopiperazin-1-yl)(phenyl) acetic acid (660 mg, 1.9 mmol) in DMF (4 ml) were added tert-butyl carbazate (278 mg, 2.1 mmol), 1-(3-dimethylaminopropyl)-3-ethylcarbodiimide hydrochloride (439 mg, 2.3 mmol), and 1-hydroxy-7-azabenzotriazole (26.0 mg, 0.19 mmol). The reaction was allowed to stir at room temperature for 18 h. The reaction was diluted with EtOAc and washed with sat'd ammonium chloride and 3M LiCl. The aqueous layers were extracted with EtOAc, and the combined organic layers were washed with 3M LiCl and brine, dried over sodium sulfate, and concentrated in vacuo to yield the Boc protected hydrazinyl amide. The crude material was dissolved in EtOAc (5 ml), saturated with HCl gas, and allowed to stir for 3 h. The reaction was concentrated in vacuo and concentrated again from methanol to yield 2-[(4-butyl-2,3-dioxopiperazin-1-yl)(phenyl)acetyl]hydrazinium chloride (75%).

Step E: Amide Coupling

To a solution of 2-[(4-butyl-2,3-dioxopiperazin-1-yl)(phenyl)acetyl]hydrazinium chloride (94.0 mg, 0.27 mmol) in 1,2-dichloroethane (2 ml) were added 1-(tert-butoxycarbonyl)-3-phenylpiperidine-2-carboxylic acid (71.0 mg, 0.23 mmol), 1-hydroxybenzotriazole (44.5 mg, 0.26 mmol), diisopropylethylamine (0.050 ml, 0.27 mmol), and polystyrene bound carbodiimide (353 mg, 0.46 mmol, 1.34 mmol/g). The reaction was allowed to stir gently at room temperature for 24 h. The reaction was filtered, concentrated, and purified via reverse phase HPLC to yield tert-butyl 2-({2-[(4-butyl-2,3- dioxopiperazin-1-yl)(phenyl)acetyl]hydrazino}carbonyl)-3-phenylpiperidine-1-carboxylate (11%).

Step F: Cyclodehydration and Boc Deprotection

To a solution of tert-butyl 2-({2-[(4-butyl-2,3-dioxopiperazin-1-yl)(phenyl)acetyl]hydrazino}carbonyl)-3-phenylpiperidine-1-carboxylate (15.5 mg, 0.026 mmol) in 1,2-dichloroethane (1.5 ml) was added Burgess reagent (21.9 mg, 0.078 mmol). The reaction vessel was sealed and heated to 120° C. for 10 min in an Emry's Optimizer microwave reactor. Additional Burgess reagent (21.9 mg, 0.078 mmol) was added to the solution, and the reaction was sealed and heated again to 120° C. for 10 min in a microwave reactor. The reaction was concentrated in vacuo to yield the cyclodehydration product. A solution of the crude material in EtOAc (5 ml) at 0° C. was saturated with HCl gas and allowed to stir for 2 h. The reaction was concentrated in vacuo and purified via reverse phase HPLC to yield 1-butyl-4-(phenyl[5-(cis-3-phenylpiperidin-2-yl)-1,3,4-oxadiazol-2-yl]methyl)piperazine-2,3-dione. HRMS (ES, M+H), cal'd for $C_{28}H_{33}N_5O_3$: 488.2656, found: 488.2646. $^1$H NMR (400 MHz, $CD_3OD$) δ 7.42-7.22 (m, 7H), 7.09 (m, 3H), 6.87 (m, 2H), 5.36 (dd, J=14.6, 5.4 Hz, 1H), 3.88 (t, J=13.2 Hz, 1H), 3.53 (m, 1H), 3.44 (m, 6H), 3.24 (m, 1H), 3.11 (m, 1H), 2.55-2.38 (m, 1H), 2.25 (m, 1H), 2.00 (m, 2H), 1.56 (m, 2H), 1.33 (sext, J=7.4 Hz, 2H), 0.94 (t, J=7.2 Hz, 3H).

The following diketopiperazine examples in Table 2 were prepared in a manner similar to Example 15.

TABLE 2

Diketopiperazine Examples

| EX | Structure | Parent MW | MS M + 4 | Stereochemistry | IUPAC Name |
|---|---|---|---|---|---|
| 16 | 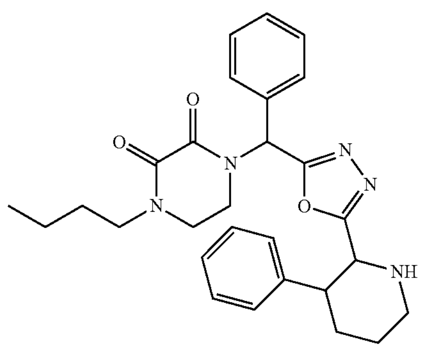 | 487.61 | 488 | RS, CIS/TRANS RACEMIC (mixt. of 8 stereoisomers) | 1-butyl-4-(phenyl{5-[3-phenylpiperidin-2-yl]-1,3,4-oxadiazol-2-yl}methyl)piperazine-2,3-dione |
| 17 | 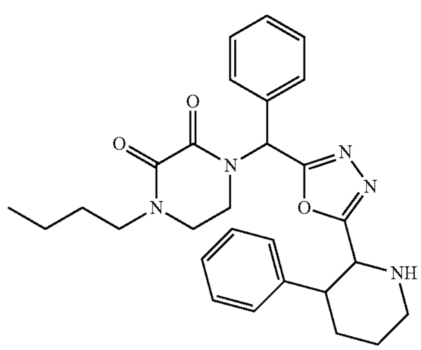 | 487.61 | 488 | RS, CIS MIXT. OF RR AND SS | 1-butyl-4-(phenyl{5-[cis-(2S,3S and 2R,3R)-3-phenylpiperidin-2-yl]-1,3,4-oxadiazol-2-yl}methyl)piperazine-2,3-dione |
| 18 | 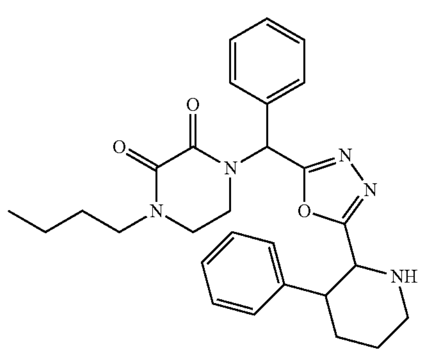 | 487.61 | 488 | RS, TRANS RS or SR | 1-butyl-4-(phenyl{5-[(trans)-3-phenylpiperidin-2-yl]-1,3,4-oxadiazol-2-yl}methyl)piperazine-2,3-dione |

TABLE 2-continued

Diketopiperazine Examples

| EX | Structure | Parent MW | MS M + 4 | Stereochemistry | IUPAC Name |
|---|---|---|---|---|---|
| 19 | 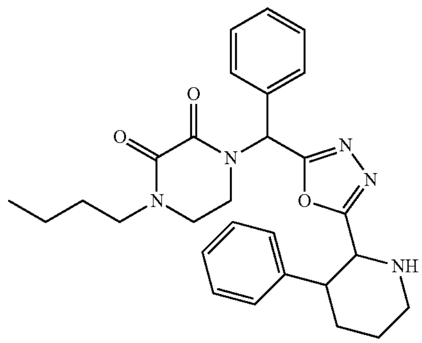 | 487.61 | 488 | RS, CIS RR OR SS | 1-butyl-4-(phenyl{5-[cis-(2S,3S or 2R,3R)-3-phenylpiperidin-2-yl]-1,3,4-oxadiazol-2-yl}methyl)piperazine-2,3-dione |

Example 20

N-methyl-N-(6-(methyl[(trans-2-methylcyclopropyl)methyl]amino)-4-[5-(cis-3-phenylpiperidin-2-yl)-1,3,4-oxadiazol-2-yl]pyridin-2-yl)methanesulfonamide
(Scheme 4A)

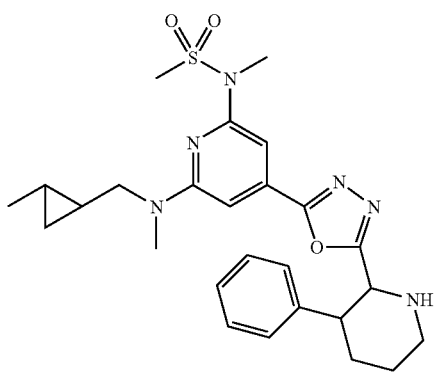

Step A: Amide Coupling

To a solution of N-[4-(hydrazinocarbonyl)-6-(methyl[(trans-2-methylcyclopropyl)methyl]amino)pyridin-2-yl]-N-methylmethanesulfonamide (3A.3b-1, 59.0 mg, 0.17 mmol) in 1,2-dichloroethane (2 ml) were added cis-1-(tert-butoxycarbonyl)-3-phenylpiperidine-2-carboxylic acid (Intermediate 1A.5, 45.9 mg, 0.15 mmol), 1-hydroxybenzotriazole (23.2 mg, 0.16 mmol), diisopropylethylamine (0.090 ml, 0.52 mmol), and polystyrene bound carbodiimide (246 mg, 0.34 mmol, 1.31 mmol/g). The reaction mixture was allowed to stir gently at room temperature for 18 h. Macroporous carbonate resin (360 mg, 0.68 mmol, 2.74 mmol/g) was added to the reaction, and the mixture was again allowed to stir gently for 18 h. The reaction mixture was filtered and concentrated in vacuo to yield tert-butyl cis-2-[(2-{2-(methyl[(trans-2-methylcyclopropyl)methyl]amino)-6-[methyl(methylsulfonyl)amino]isonicotinoyl}hydrazino)carbonyl]-3-phenylpiperidine-1-carboxylate.

Step B: Cyclodehydration and Boc Deprotection

To a solution of tert-butyl cis-2-[(2-{2-(methyl[(trans-2-methylcyclopropyl)methyl]amino)-6-[methyl(methylsulfonyl)amino]isonicotinoyl}hydrazino)carbonyl]-3-phenylpiperidine-1-carboxylate (93.7 mg, 0.15 mmol) in 1,2-dichloroethane (1.5 ml) was added Burgess reagent (162 mg, 0.60 mmol). The reaction vessel was sealed and heated to 120° C. for 10 min in an Emry's Optimizer microwave reactor. The reaction was concentrated in vacuo and purified via reverse phase HPLC to yield the cyclodehydration product. A solution of the material in EtOAc (15 ml) at 0° C. was saturated with HCl gas and allowed to stir for 1 h. The reaction was concentrated in vacuo and purified via reverse phase HPLC to yield title example N-methyl-N-(6-(methyl[(trans-2-methylcyclopropyl)methyl]amino)-4-[5-(cis-3-phenylpiperidin-2-yl)-1,3,4-oxadiazol-2-yl]pyridin-2-yl)methanesulfonamide. HRMS (ES, M+H), cal'd for $C_{26}H_{34}N_6O_3S$: 511.2486. found: 511.2475. $^1$H NMR (400 MHz, $CD_3OD$) δ 7.32 (m, 3H), 7.19 (d, J=7.3 Hz, 2H), 6.78 (m, 1H), 6.55 (m, 1H), 5.45 (d, J=5.1 Hz, 1H), 3.99 (m, 1H), 3.62 (m, 1H), 3.54 (m, 2H), 3.38 (m, 1H), 3.34 (s, 3H), 3.14 (s, 3H), 3.10 (s, 3H), 2.43-2.27 (m, 2H), 2.03 (m, 2H), 1.04 (d, J=5.7 Hz, 3H), 0.73 (m, 2H), 0.46 (m, 1H), 0.26 (m, 1H).

The following pyridylamine examples were prepared in a manner similar to Example 20 (Scheme 4A, starting with 3A.3b and ending with structures of type 4A.2b) or through an intermediate of type 3A.3a (Schemes 3A and 4A) involving a late stage Pd-catalyzed amination (using amines from Scheme 2 and intermediates of type 4A.1a) prior to final deprotection of 4A.1b to give additional examples of type 4A.2b. Examples bearing a 5-chloro were prepared directly from the protio precursor examples of type 4A.2b via treatment with N-chlorosuccinimide (1.0 equiv) at rt in dichloromethane in a manner similar to that described in WO 2006/057945 (Example 1 pg. 66). Various starting Boc protected cyclic amino acid Intermediate 1A.5, 1A.6 or analogs thereof were used throughout.

TABLE 3

Pyridylamine Example

| EX | Structure | Parent MW | MS M + 4 | Stereochemistry | IUPAC Name |
|----|-----------|-----------|----------|-----------------|------------|
| 21 | 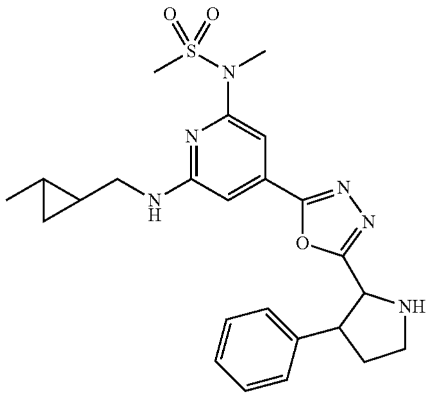 | 482.6 | 483 | TRANS SS and RR, CIS SS and RR (mixt. of 4 stereoisomers) | N-methyl-N-(6-(methyl[(trans-2-methylcyclopropyl)methyl]amino)-4-[5-(cis-3-phenylpiperidin-2-yl)-1,3,4-oxadiazol-2-yl]pyridin-2-yl)methanesulfonamide |
| 22 | 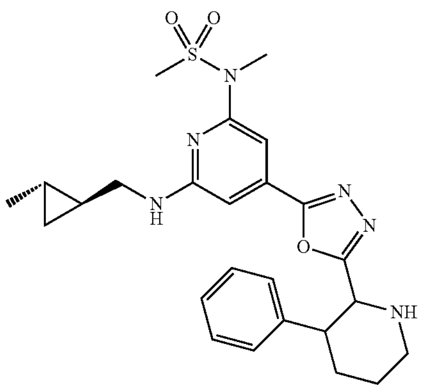 | 496.64 | 497 | TRANS SS, CIS SS and RR | N-methyl-N-(6-({[(1S,2S)-2-methylcyclopropyl]methyl}amino)-4-{5-[cis-3-phenylpiperidin-2-yl]-1,3,4-oxadiazol-2-yl}pyridin-2-yl)methanesulfonamide |
| 23 | 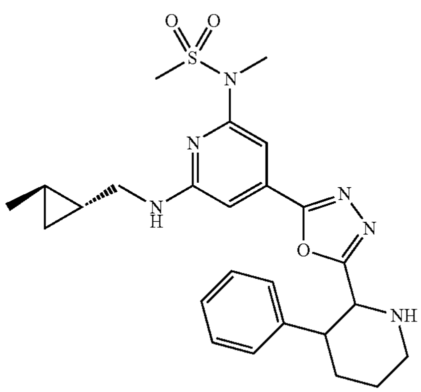 | 496.64 | 497 | TRANS RR, CIS SS and RR | N-methyl-N-(6-({[(1R,2R)-2-methylcyclopropyl]methyl}amino)-4-{5-[cis-3-phenylpiperidin-2-yl]-1,3,4-oxadiazol-2-yl}pyridin-2-yl)methanesulfonamide |
| 24 | 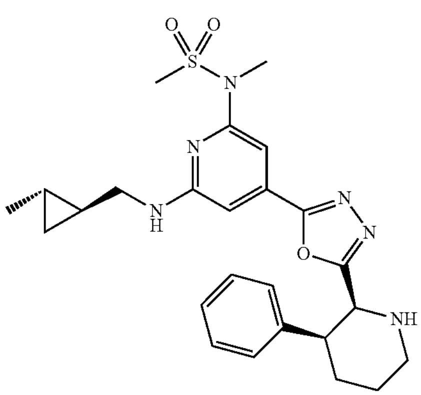 | 496.64 | 497 | TRANS SS, CIS SS or RR | N-methyl-N-(6-({[(1S,2S)-2-methylcyclopropyl]methyl}amino)-4-{5-[cis-(2S,3S or 2R,3R)-3-phenylpiperidin-2-yl]-1,3,4-oxadiazol-2-yl}pyridin-2-yl)methanesulfonamide |

TABLE 3-continued

Pyridylamine Example

| EX | Structure | Parent MW | MS M + 4 | Stereochemistry | IUPAC Name |
|---|---|---|---|---|---|
| 25 | 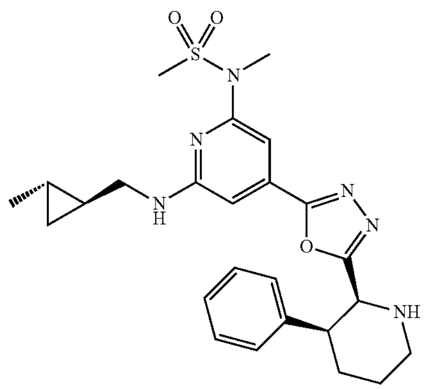 | 496.64 | 497 | TRANS SS, CIS RR or SS | N-methyl-N-(6-({[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)methanesulfonamide |
| 26 | 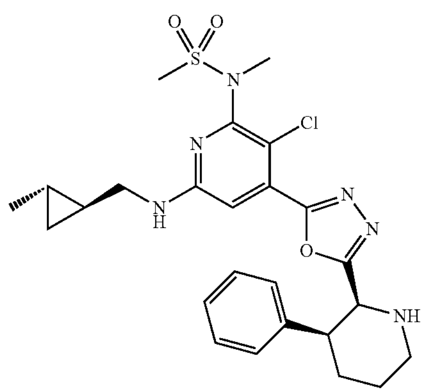 | 531.08 | 532 | TRANS SS, CIS RR or SS | N-(3-chloro-6-({[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)-N-methylmethanesulfonamide |
| 27 | 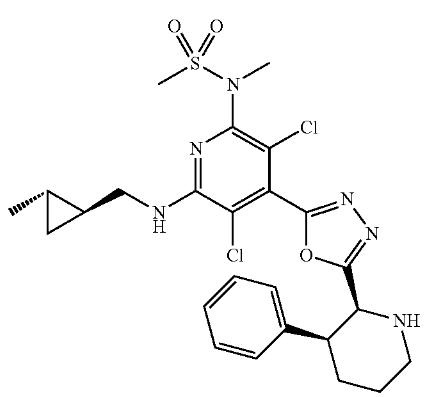 | 565.53 | 566 | TRANS SS, CIS RR or SS | N-(3,5-dichloro-6-({[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)-N-methylmethanesulfonamide |

TABLE 3-continued

Pyridylamine Example

| EX | Structure | Parent MW | MS M + 4 | Stereochemistry | IUPAC Name |
|---|---|---|---|---|---|
| 28 | 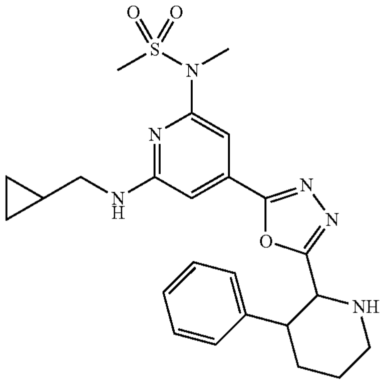 | 482.61 | 483 | CIS RR and SS | N-(6-[(cyclopropylmethyl)amino]-4-{5-[cis-3-phenylpiperidin-2-yl]-1,3,4-oxadiazol-2-yl}pyridin-2-yl)-N-methylmethanesulfonamide |
| 29 | 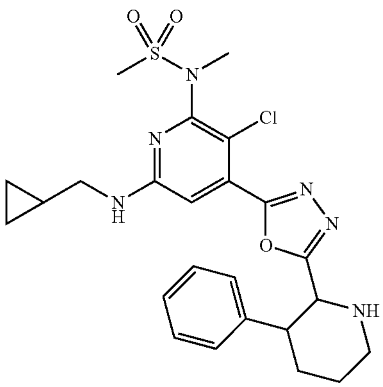 | 517.05 | 518 | CIS RR and SS | N-(3-chloro-6-[(cyclopropylmethyl)amino]-4-{5-[cis-3-phenylpiperidin-2-yl]-1,3,4-oxadiazol-2-yl}pyridin-2-yl)-N-methylmethanesulfonamide |
| 30 | 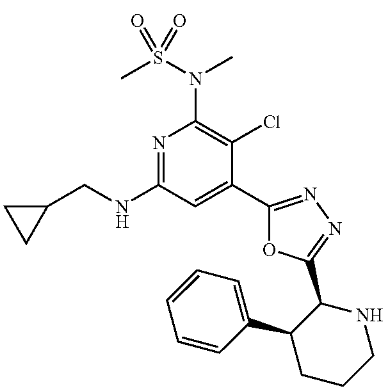 | 517.05 | 518 | CIS SS or RR | N-(3-chloro-6-[(cyclopropylmethyl)amino]-4-{5-[(2S,3S or 2R,3R)-3-phenylpiperidin-2-yl]-1,3,4-oxadiazol-2-yl}pyridin-2-yl)-N-methylmethanesulfonamide |
| 31 | 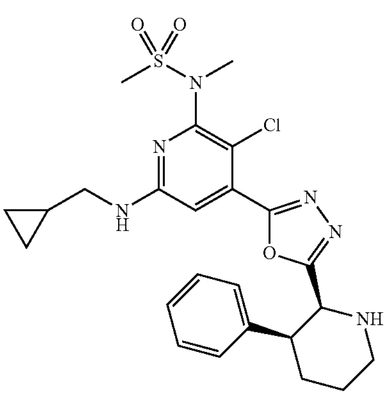 | 517.05 | 518 | CIS RR or SS | N-(3-chloro-6-[(cyclopropylmethyl)amino]-4-{5-[(2S,3S or 2R,3R)-3-phenylpiperidin-2-yl-1,3,4-oxadiazol-2-yl}pyridin-2-yl)-N-methylmethanesulfonamide |

TABLE 3-continued

Pyridylamine Example

| EX | Structure | Parent MW | MS M + 4 | Stereochemistry | IUPAC Name |
|---|---|---|---|---|---|
| 32 | 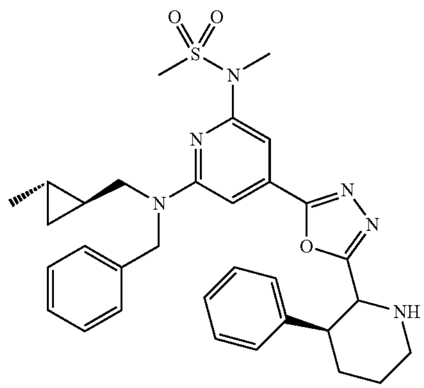 | 586.76 | 587 | TRANS SS, TRANS SR and RS | N-(6-(benzyl{[(1S,2S)-2-methylcyclopropyl]methyl}amino)-4-{5-[(2S,3R and 2R.3S)-3-phenylpiperidin-2-yl)-1,3,4-oxadiazol-2-yl}pyridin-2-yl)-N-methylmethanesulfonamide |
| 33 | 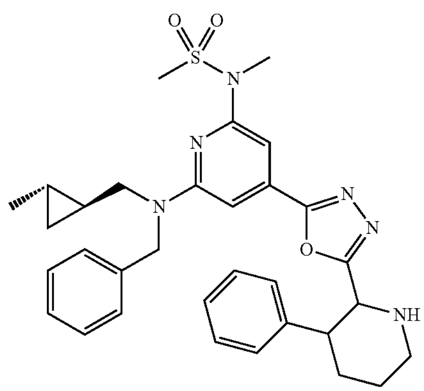 | 586.76 | 587 | TRANS SS, CIS SS and RR | N-(6-(benzyl{[(1S,2S)-2-methylcyclopropyl]methyl}amino)-4-{5-[cis-3-phenylpiperidin-2-yl]-1,3,4-oxadiazol-2-yl}pyridin-2-yl)-N-methylmethanesulfonamide |
| 34 | 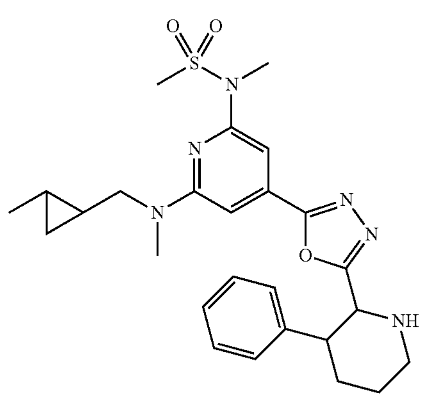 | 510.66 | 511 | TRANS RR amd SS, TRANS SR and RS (4 stereoisomers) | N-methyl-N-(6-{methyl[trans-(2-methylcyclopropyl)methyl]amino}-4-{5-[trans-3-phenylpiperidin-2-yl]-1,3,4-oxadiazol-2-yl}pyridin-2-yl)methanesulfonamide |

TABLE 3-continued

Pyridylamine Example

| EX | Structure | Parent MW | MS M + 4 | Stereochemistry | IUPAC Name |
|---|---|---|---|---|---|
| 35 | 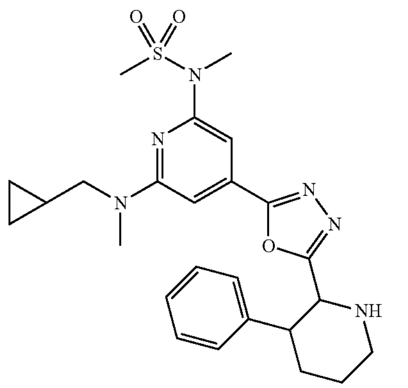 | 496.64 | 497 | CIS RR and SS | N-(6-[(cyclopropylmethyl)(methyl)amino]-4-{5-[cis-3-phenylpiperidin-2-yl]-1,3,4-oxadiazol-2-yl}pyridin-2-yl)-N-methylmethanesulfonamide |
| 36 | 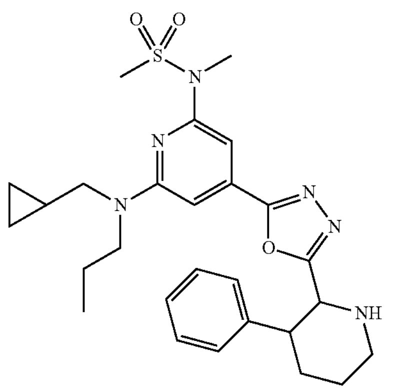 | 524.69 | 525 | CIS RR and SS | N-(6-[(cyclopropylmethyl)(propyl)amino]-4-{5-[cis-3-phenylpiperidin-2-yl]-1,3,4-oxadiazol-2-yl}pyridin-2-yl)-N-methylmethanesulfonamide |
| 37 | 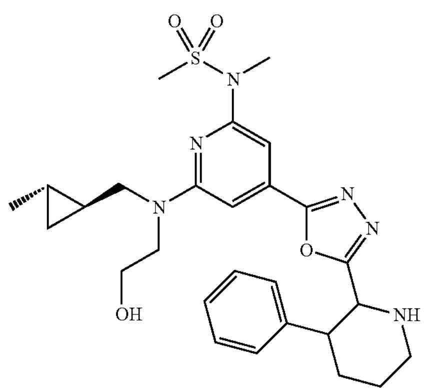 | 540.69 | 541 | TRANS SS, CIS RR and SS | N-(6-((2-hydroxyethyl){[(1S,2S)-2-methylcyclopropyl]methyl}amino)-4-{5-[(2S,3S and 2R,3R)-3-phenylpiperidin-2-yl]-1,3,4-oxadiazol-2-yl}pyridin-2-yl)-N-methylmethanesulfonamide |
| 38 | 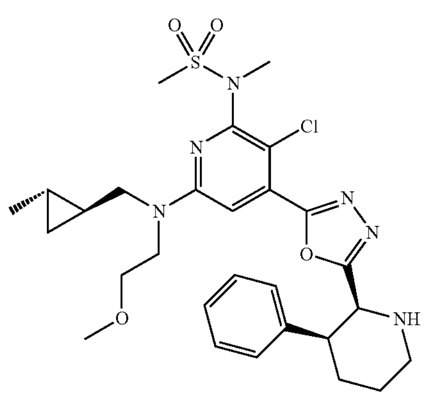 | 589.16 | 590 | TRANS SS, CIS RR or SS | N-(3-chloro-6-((2-methoxyethyl){[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)-N-methylmethanesulfonamide |

TABLE 3-continued

Pyridylamine Example

| EX | Structure | Parent MW | MS M + 4 | Stereochemistry | IUPAC Name |
|---|---|---|---|---|---|
| 39 | 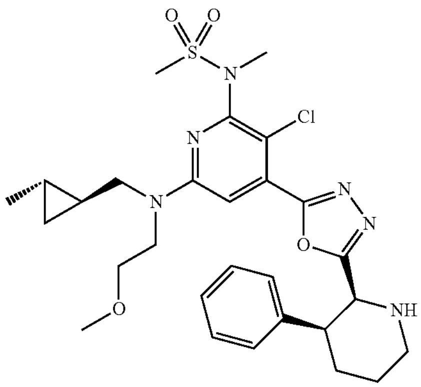 | 589.16 | 590 | TRANS SS, CIS RR or SS | N-(3-chloro-6-((2-methoxyethyl){[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)-N-methylmethanesulfonamide |
| 40 | 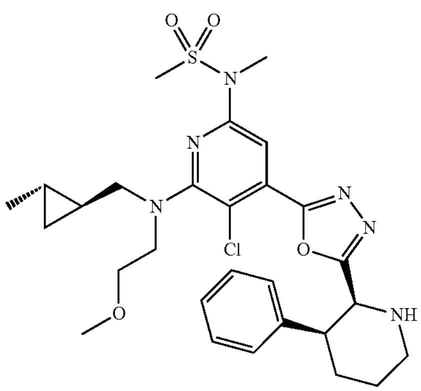 | 589.16 | 590 | TRANS SS, CIS RR or SS | N-(5-chloro-6-((2-methoxyethyl){[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)-N-methylmethanesulfonamide |
| 41 | 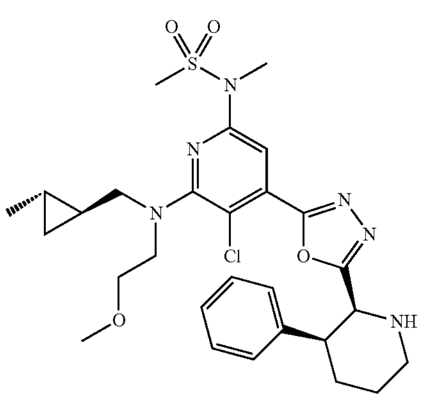 | 589.16 | 590 | TRANS SS, CIS RR or SS | N-(5-chloro-6-((2-methoxyethyl){[(1S,2S)-2-methylcyclopropyl]methyl}amino)-4-{5-[(2S,3S or 2R,3R)-3-phenylpiperidin-2-yl]-1,3,4-oxadiazol-2-yl}pyridin-2-yl)-N-methylmethanesulfonamide |

TABLE 3-continued

Pyridylamine Example

| EX | Structure | Parent MW | MS M + 4 | Stereochemistry | IUPAC Name |
|---|---|---|---|---|---|
| 42 | 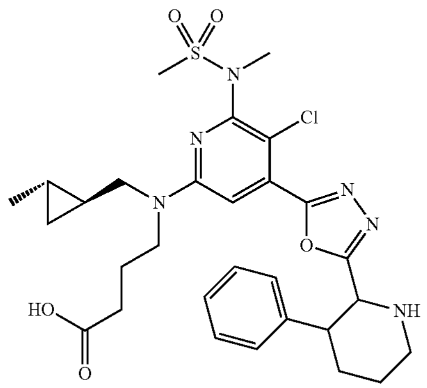 | 617.17 | 618 | TRANS SS, CIS RR or SS | 4-((5-chloro-6-[methyl(methylsulfonyl)amino]-4-{5-[cis-3-phenylpiperidin-2-yl]-1,3,4-oxadiazol-2-yl}pyridin-2-yl){[(1S,2S)-2-methylcyclopropyl]methyl}amino)butanoic acid |
| 43 | 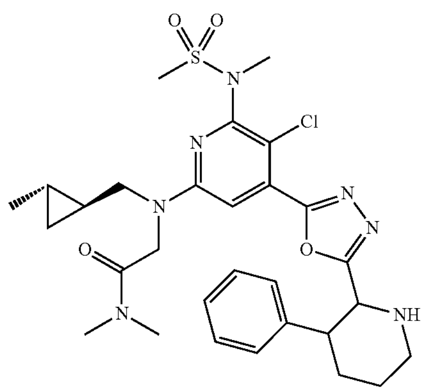 | 616.19 | 617 | TRANS SS, TRANS RS and SR | $N^2$-(5-chloro-6-[methyl(methylsulfonyl)amino]-4-{5-[trans-3-phenylpiperidin-2-yl]-1,3,4-oxadiazol-2-yl}pyridin-2-yl)-N,N-dimethyl-$N^2$-{[(1S,2S)-2-methylcyclopropyl]methyl}glycinamide |
| 44 | 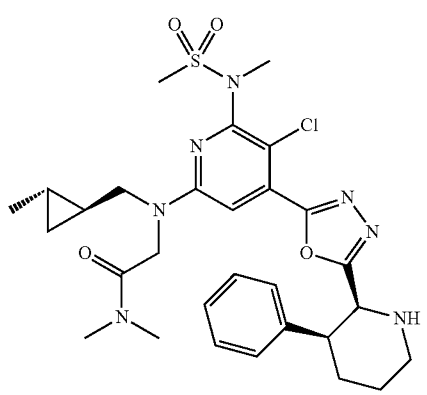 | 616.19 | 617 | TRANS SS, CIS (2S,3S) | $N^2$-(5-chloro-6-[methyl(methylsulfonyl)amino]-4-{5-[(2S,3S)-3-phenylpiperidin-2-yl]-1,3,4-oxadiazol-2-yl}pyridin-2-yl)-N,N-dimethyl-$N^2$-{[(1S,2S)-2-methylcyclopropyl]methyl}glycinamide |
| 45 | 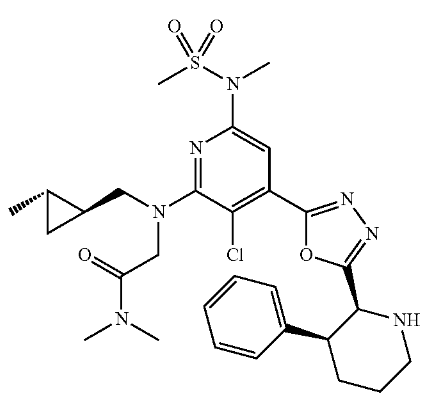 | 616.19 | 617 | TRANS SS, CIS (2S,3S) | $N^2$-(3-chloro-6-[methyl(methylsulfonyl)amino]-4-{5-[(2S,3S)-3-phenylpiperidin-2-yl]-1,3,4-oxadiazol-2-yl}pyridin-2-yl)-N,N-dimethyl-$N^2$-{[(1S,2S)-2-methylcyclopropyl]methyl}glycinamide |

TABLE 3-continued

Pyridylamine Example

| EX | Structure | Parent MW | MS M + 4 | Stereochemistry | IUPAC Name |
|---|---|---|---|---|---|
| 46 | 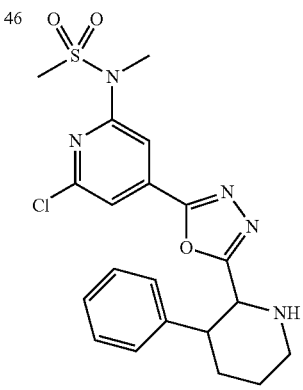 | 447.95 | 448 | CIS RR and SS | N-(6-chloro-4-{5-[cis-3-phenylpiperidin-2-yl]-1,3,4-oxadiazol-2-yl}pyridin-2-yl)-N-methylmethanesulfonamide |
| 47 | 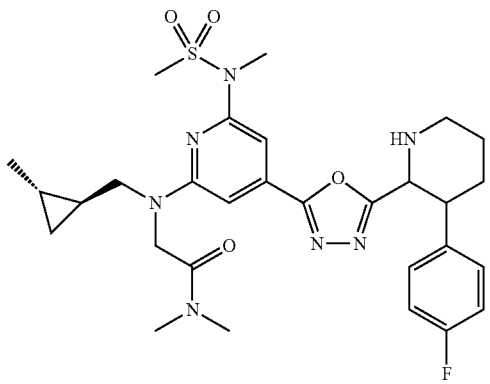 | 599.7 | 600 | TRANS SS, CIS RR and SS | cis-$N^2$-{4-{5-[(2S,3S)-3-(4-fluorophenyl)piperidin-2-yl]-1,3,4-oxadiazol-2-yl}-6-[methyl(methylsulfonyl)amino]pyridin-2-yl}-N,N-dimethyl-$N^2$-{[(1S,2S)-2-methylcyclopropyl]methyl}glycinamide |
| 48 | 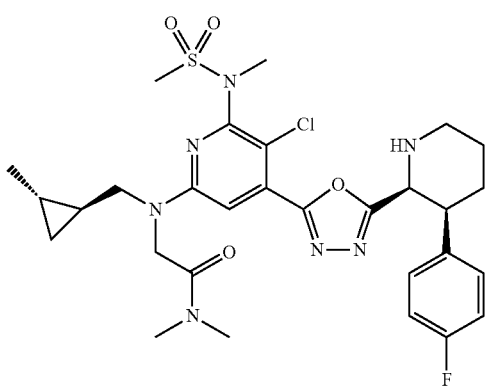 | 634.1 | 635 | TRAS SS, CIS (2S, 3S) | $N^2$-{5-chloro-4-{5-[(2S,3S)-3-(4-fluorophenyl)piperidin-2-yl]-1,3,4-oxadiazol-2-yl}-6-[methyl(methylsulfonyl)amino]pyridin-2-yl}-N,N-dimethyl-$N^2$-{[(1S,2S)-2-methylcyclopropyl]methyl}glycinamide |

Examples of type 4B.2a and 4B.2b were prepared in manner similar to example 20 (Scheme 4B) starting from appropriately functionalized acylhydrazides of type 3B.3a and 3B.3b which are prepared using Boc-hydrazide and the appropriate starting isophthalic carboxylic acids as described in WO 2004/043916:

TABLE 4

Phenylamide Examples

| EX | Structure | Parent MW | MS M + 4 | Stereochemistry | INPAC Name |
|---|---|---|---|---|---|
| 49 | 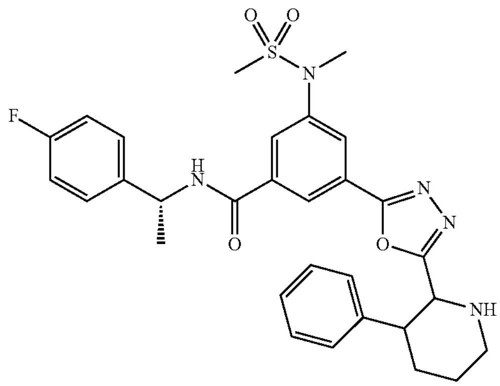 | 577.68 | 578 | R, CIS RR and SS | N-[(1R)-1-(4-fluorophenyl)ethyl]-3-[meethyl(sulfonyl)amino]-5-{5-[cis-3-phenylpiperidin-2-yl]-1,3,4-oxadiazol-2-yl}benzamide |
| 50 | 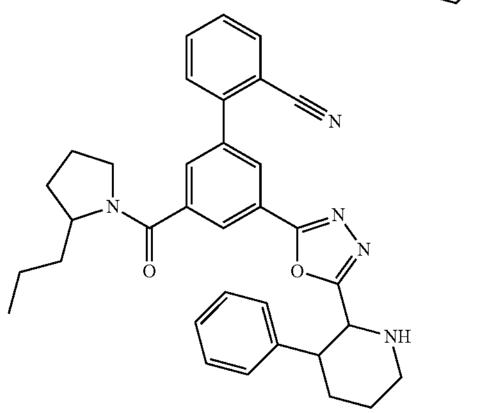 | 545.69 | 546 | R and S, CIS RR and SS (mixt. of four stereoisomers) | 3'-{5-[cis-3-phenylpiperidin-2-yl]-1,3,4-oxadiazol-2-yl}-5'-[(2-propylpyrrolidin-1-yl)carbonyl]-1,1'-biphenyl-2-carbonitrile |
| 51 | 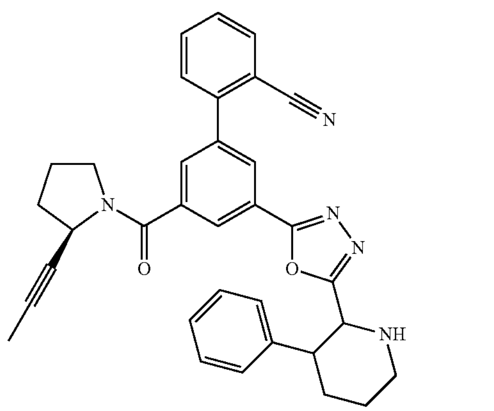 | 541.66 | 542 | R, CIS RR and SS | 3'-{5-[cis-3-phenylpiperidin-2-yl]-1,3,4-oxadiazol-2-yl}-5'-{[(2R)-2-prop-1-ynylpyrrolidin-1-yl]carbonyl}-2,2'-biphenyl-2-carbonitrile |
| 52 | 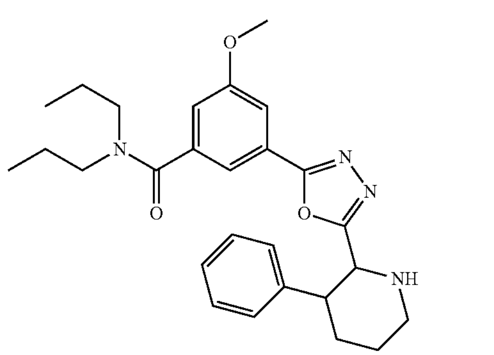 | 462.60 | 463 | CIS RR and SS | 3-methoxy-5-{5-[cos-3-phenylpiperidin-2-yl]-1,3,4-oxadiazol-2-yl}-N,N-dipropylbenzamide |

Example 53 cis-N-({2-((2-methoxyethyl){[trans-(1S,2S)-2-methylcyclopropyl]methyl}amino)-6-[methyl(methylsulfonyl)amino]pyridin-4-yl}methyl)-3-phenylpiperidine-2-carboxamide

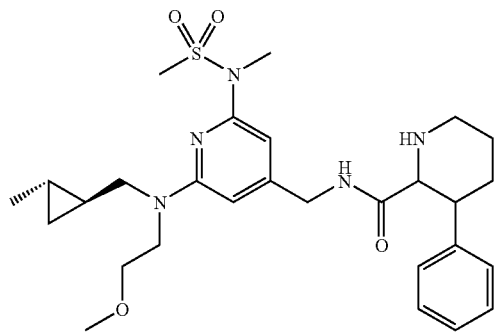

Step A: Carboxylic Acid Reduction

To a solution of 2-((2-methoxyethyl){[trans-(1S,2S)-2-methylcyclopropyl]methyl}amino)-6-[methyl(methylsulfonyl)amino]isonicotinic acid (202 mg, 0.544 mmol) in THF (3 ml) at 0° C. was added 1M borane-THF complex in THF (1.63 ml, 1.63 mmol). The reaction was warmed to rt and allowed to stir for 18 h. The reaction was quenched with MeOH and concentrated in vacuo to yield N-[4-(hydroxymethyl)-6-((2-methoxyethyl){[trans-(1S,2S)-2-methylcyclopropyl]methyl}amino)pyridin-2-yl]-N-methylmethanesulfonamide (100%). HRMS (ES, M+H) calc'd for $C_{16}H_{27}N_3O_4S$: 358.1795. found: 358.1796. $^1$H NMR (400 MHz, $CD_3OD$) δ 6.51 (d, J=5.3 Hz, 2H), 4.55 (s, 2H), 3.74 (m, 2H), 3.59 (m, 3H), 3.49 (m, 1H), 3.37-3.33 (m, 1H), 3.35 (s, 3H), 3.13 (s, 3H), 1.04 (d, J=6.1 Hz, 3H), 0.84-0.70 (m, 2), 0.47-0.43 (m, 1H), 0.28-0.23 (m, 1H).

Step B: Chloride Preparation

To a solution of N-[4-(hydroxymethyl)-6-((2-methoxyethyl){[trans-(1S,2S)-2-methylcyclopropyl]methyl}amino)pyridin-2-yl]-N-methylmethanesulfonamide (220 mg, 0.615 mmol) in dichloromethane (4 ml) at 0° C. were added triethylamine (0.12 ml, 0.861 mmol) and methane sulfonyl chloride (0.063 ml, 0.800 mmol). The reaction was warmed to rt and allowed to stir for 18 h. The reaction was diluted with dichloromethane, washed with water (3×) and brine (1×), dried over sodium sulfate, filtered, and concentrated in vacuo to yield N-[4-(chloromethyl)-6-((2-methoxyethyl){[trans-(1S,2S)-2-methylcyclopropyl]methyl}amino)pyridin-2-yl]-N-methylmethanesulfonamide (100%).

Step C: Azide Preparation

To a solution of N-[4-(chloromethyl)-6-((2-methoxyethyl){[trans-(1S,2S)-2-methylcyclopropyl]methyl}amino)pyridin-2-yl]-N-methylmethanesulfonamide (106 mg, 0.281 mmol) in DMF (2 ml) were added sodium iodide (43.3 mg, 0.281 mmol) and sodium azide (77.5 mg, 1.12 mmol). The reaction mixture was heated to 40° C. and allowed to stir for 2 h. The reaction mixture was concentrated in vacuo and purified via flash chromatography (silica, 0-30% EtOAc/hexanes) to yield N-[4-(azidomethyl)-6-((2-methoxyethyl){[trans-(1S,2S)-2-methylcyclopropyl]methyl}amino)pyridin-2-yl]-N-methylmethanesulfonamide (60%).

Step D: Azide Reduction

To a solution of N-[4-(azidomethyl)-6-((2-methoxyethyl){[trans-(1S,2S)-2-methylcyclopropyl]methyl}amino)pyridin-2-yl]-N-methylmethanesulfonamide (64.0 mg, 0.167 mmol) in ethanol (3 ml) was added 10% palladium on carbon (15.9 mg, 0.033 mmol). The reaction was charged with 1 atm hydrogen gas and allowed to stir for 18 h. The reaction mixture was filtered through celite, and the filtrate was concentrated in vacuo to yield N-[4-(aminomethyl)-6-((2-methoxyethyl){[trans-(1S,2S)-2-methylcyclopropyl]methyl}amino)pyridin-2-yl]-N-methylmethanesulfonamide (82%).

Step E: Amide Coupling and Boc Deprotection

To a solution of N-[4-(aminomethyl)-6-((2-methoxyethyl){[trans-(1S,2S)-2-methylcyclopropyl]methyl}amino)pyridin-2-yl]-N-methylmethanesulfonamide (48.7 mg, 0.137 mmol) in DMF (1 ml) were added cis-1-(tert-butoxycarbonyl)-3-phenylpiperidine-2-carboxylic acid (44.7 mg, 0.137 mmol), benzotriazol-1-yloxytris(dimethylamino)phosphonium hexafluorophospate (85.4 mg, 0.164 mmol), and diisopropylethylamine (0.024 ml, 0.137 mmol). The reaction was allowed to stir for 1 h, and then it was purified via reverse phase preparative HPLC to yield the Boc protected product. The material was dissolved in 1:2 TFA/dichloromethane (3 ml) and allowed to stir for 1 h. The reaction was concentrated in vacuo and purified via reverse phase preparative HPLC to yield cis-N-({2-((2-methoxyethyl){[trans-(1S,2S)-2-methylcyclopropyl]methyl}amino)-6-[methyl(methylsulfonyl)amino]pyridin-4-yl}methyl)-3-phenylpiperidine-2-carboxamide. HRMS (ES, M+H) calc'd for $C_{28}H_{41}N_5O_4S$: 544.2952. found: 544.2969. $^1$H NMR (400 MHz, $CD_3OD$) δ 8.04 (t, J=5.1 Hz, 1H), 7.25 (m, 3H), 7.18 (m, 2H), 6.17 (s, 1H), 5.97 (s, 1H), 4.06 (m, 1H), 3.87 (m, 1H), 3.77 (d, J=11.4 Hz, 1H), 3.69 (t, J=6.0 Hz, 2H), 3.57 (t, J=6.2 Hz, 2H), 3.44 (m, 2H), 3.34 (s, 3H), 3.25 (s, 3H), 3.17 (m, 4H), 3.02 (m, 1H), 1.99 (m, 4H), 1.04 (d, J=6.0 Hz, 3H), 0.79-0.69 (m, 2H), 0.44 (m, 1H), 0.25 (m, 1H).

Example 54

2-((2-methoxyethyl){[trans-(1S,2S)-2-methylcyclopropyl]methyl}amino)-6-[methyl(methylsulfonyl)amino]-N-[(cis-3-phenylpiperidin-2-yl)methyl]isonicotinamide

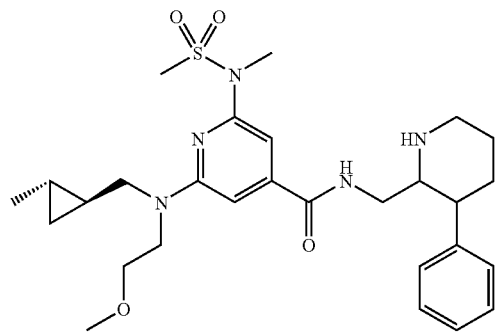

To a solution of 2-((2-methoxyethyl){[trans-(1S,2S)-2-methylcyclopropyl]methyl}amino)-6-[methyl(methylsulfonyl)amino]isonicotinic acid (84.9 mg, 0.229 mmol) in DMF (1.5 ml) were added cis-2-(ammoniomethyl)-3-phenylpiperidinium dichloride (58.0 mg, 0.240 mmol), 1-(3-dimethylaminopropyl)-3-ethylcarbodiimide hydrochloride (74.4 mg, 0.321 mmol), 1-hydroxybenzotriazole (38.8 mg, 0.252 mmol), and diisopropylethylamine (99.6 mg, 0.572 mmol). The reaction was allowed to stir for 1 h, and then it was purified via reverse phase preparative HPLC to yield 2-((2- methoxyethyl){[trans-(1S,2S)-2-methylcyclopropyl]methyl}amino)-6-[methyl(methylsulfonyl)amino]-N-[(cis-3-phenylpiperidin-2-yl)methyl]isonicotinamide (19%). HRMS (ES, M+H) calc'd for $C_{28}H_{41}N_5O_4S$: 544.2952. found: 544.2987. $^1$H NMR (400 MHz, $CD_3OD$) δ 7.43-7.29 (m, 6H), 6.83 (d, J=9.3 Hz, 1H), 6.77 (d, J=18.9 Hz, 1H), 4.12 (m, 0.5H), 3.91 (m, 0.5H), 3.75 (q, J=6.3 Hz, 2H), 3.67-3.56 (m, 2H), 3.54-3.47 (m, 2H), 3.33 (s, 3H), 3.30 (s, 3H), 3.14 (d, J=3.7 Hz, 3H), 3.06 (m, 2H), 2.83 (t, J=11.5 Hz, 1H), 2.23 (m, 1H), 2.01-1.85 (m, 4H), 1.03 (m, 3H), 0.75 (m, 2H), 0.45 (m, 1H), 0.25 (m, 1H).

Example 55

N-[6-((2-methoxyethyl){[trans-(1S,2S)-2-methylcyclopropyl]methyl}amino)-4-([(cis-3-phenylpiperidin-2-yl)methoxy]methyl)pyridin-2-yl]-N-methylmethanesulfonamide

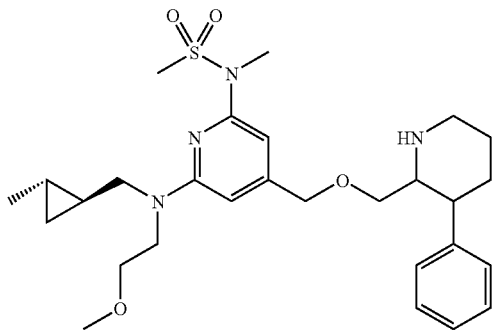

Step A: Bromide Preparation

To a solution of N-[4-(hydroxymethyl)-6-((2-methoxyethyl){[trans-(1S,2S)-2-methylcyclopropyl]methyl}amino)pyridin-2-yl]-N-methylmethanesulfonamide (208 mg, 0.581 mmol) in dichloromethane (3 ml) at 0° C. were added carbon tetrabromide (244 mg, 0.697 mmol) and polystyrene bound triphenyl phosphine (294 mg, 0.697 mmol, 2.04 mmol/g). The reaction was allowed to stir for 18 h, at which point additional carbon tetrabromide (120 mg, 0.290 mmol) and polystyrene bound triphenyl phosphine (289 mg, 0.290 mmol) were added to the reaction. The reaction mixture was allowed to stir for an additional 24 h and was then filtered and concentrated in vacuo. The crude material was purified via flash chromatography (silica, 0-40% EtOAc/hexanes) to yield N-[4-(bromomethyl)-6-((2-methoxyethyl){[trans-(1S,2S)-2-methylcyclopropyl]methyl}amino)pyridin-2-yl]-N-methylmethanesulfonamide (54%). HRMS (ES, M+H) calc'd for $C_{16}H_{26}BrN_3O_3S$: 420.0951. found: 420.0964.

Step B: Ether Formation and Boc Deprotection

To a solution of tert-butyl cis-2-(hydroxymethyl)-3-phenylpiperidine-1-carboxylate (51.6 mg, 0.177 mmol) and 4A molecular sieves in anhydrous dichloromethane (2 ml) at 0° C. was added 2,6-di-tert-butylpyridine (0.064 ml, 0.283 mmol). The mixture was allowed to stir for 10 min, and then N-[4-(bromomethyl)-6-((2-methoxyethyl){[trans-(1S,2S)-2-methylcyclopropyl]methyl}amino)pyridin-2-yl]-N-methylmethanesulfonamide (88.0 mg, 0.212 mmol) and silver trifluoromethane sulfonate (80.4 mg, 0.265 mmol) were added to the reaction. The reaction mixture was allowed to stir for 18 h, then it was filtered, concentrated in vacuo, and purified via reverse phase preparative HPLC to yield the Boc protected product. The material was dissolved in 1:1 TFA/dichloromethane (2 ml) and allowed to stir for 1 h. The reaction was concentrated in vacuo and purified via reverse phase preparative HPLC to yield N-[6-((2-methoxyethyl){[trans-(1S,2S)-2-methylcyclopropyl]methyl}amino)-4-([(cis-3-phenylpiperidin-2-yl)methoxy]methyl)pyridin-2-yl]-N-methylmethanesulfonamide. HRMS (ES, M+H) calc'd for $C_{28}H_{42}N_4O_4S$: 531.3000. found: 531.3039. $^1$H NMR (400 MHz, $CD_3OD$) δ 7.37-7.22 (m, 5H), 6.51 (s, 1H), 6.37 (s, 1H), 4.46-4.33 (m, 2H), 3.91 (m, 1H), 3.85 (q, J=10.3 Hz, 1H), 3.71 (m, 2H), 3.57 (m, 2H), 3.46 (m, 1H), 3.38-3.24 (overlapping m, 4H), 3.33 (s, 3H), 3.28 (s, 3H), 3.19 (m, 1H), 3.07 (s, 3H), 2.26-2.10 (m, 2H), 2.04-1.84 (m, 2H), 1.03 (d, J=5.9 Hz, 3H), 0.77-0.67 (m, 2H), 0.43 (m, 1H), 0.24 (m, 1H).

Example 56

{2-((2-methoxyethyl){[trans-(1S,2S)-2-methylcyclopropyl]methyl}amino)-6-[methyl(methylsulfonyl)amino]pyridin-4-yl}methyl cis-3-phenylpiperidine-2-carboxylate

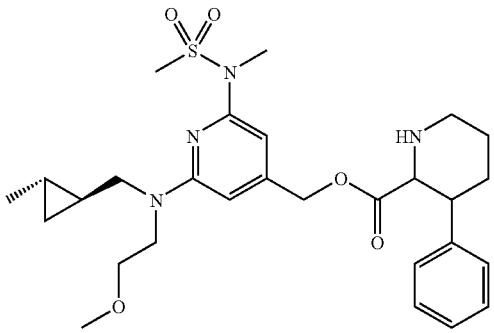

To a solution of N-[4-(chloromethyl)-6-((2-methoxyethyl){[trans-(1S,2S)-2-methylcyclopropyl]methyl}amino)pyridin-2-yl]-N-methylmethanesulfonamide (106 mg, 0.281 mmol) in degassed DMF (2 ml) were added cis-1-(tert-butoxycarbonyl)-3-phenylpiperidine-2-carboxylic acid (102 mg, 0.309 mmol), cesium carbonate (104 mg, 0.309 mmol), and sodium iodide (55.9 mg, 0.281 mmol). The reaction was allowed to stir for 24 h, and then it was purified via reverse phase preparative HPLC to yield the Boc protected material. The material was dissolved in 1:2 TFA/dichloromethane (7.5 ml) and allowed to stir for 1 h. The reaction was concentrated in vacuo and purified via reverse phase preparative HPLC to yield {2-((2-methoxyethyl){[trans-(1S,2S)-2-methylcyclopropyl]methyl}amino)-6-[methyl(methylsulfonyl)amino]pyridin-4-yl}methyl cis-3-phenylpiperidine-2-carboxylate. HRMS (ES, M+H), calc'd for $C_{28}H_{40}N_4O_5S$: 545.2792. found 545.2742. $^1$H NMR (400 MHz, $CD_3OD$) δ 7.28-7.20 (m, 5H), 6.17 (d, J=6.0 Hz, 2H), 4.87 (m, 4H), 4.59 (d, J=5.5 Hz, 1H), 3.70 (m, 3H), 3.59-3.41 (m, 4H), 3.34 (s, 3H), 3.27 (s, 3H), 3.12 (s, 3H), 2.19-2.04 (m, 3m), 1.87 (m, 1H), 1.04 (d, J=5.9 Hz, 3H), 0.73 (m, 2H), 0.44 (m, 1H), 0.26 (m, 1H).

TABLE 5

Pyridylamine Compounds
The following examples were prepared in an analogous manner to examples 46-49 using intermediates of type 3A.2b and related.

| EX | Structure | Parent MW | MS M+H | Stereochemistry | IUPAC NAME |
|----|-----------|-----------|--------|-----------------|------------|
| 57 | 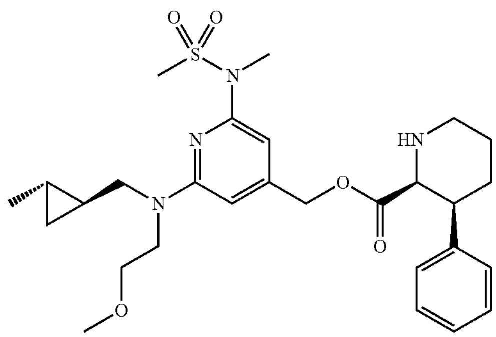 | 544.72 | 545 | TRANS SS, CIS RR or SS | {2-((2-methoxyethyl){[(1S,2S)-2-methylcyclopropyl]methyl]amino)-6-[methyl(methylsulfonyl)amino]pyridin-4-yl}methyl (2S,3S or 2R,3R)-3-phenylpiperidine-2-carboxylate |
| 58 | 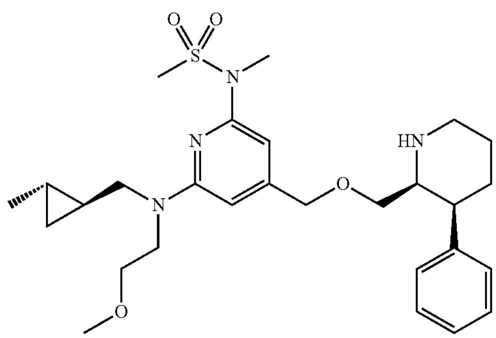 | 530.74 | 531 | TRANS SS, CIS RR or SS | N-[6-((2-methoxyethyl){[(1S,2S)-2-methylcyclopropyl]methyl}amino)-4-({[(2S,3S or 2R,3R)-3-phenylpiperidin-2-yl]methoxy}methyl)pyridin-2-yl]-N-methylmethanesulfonamide |
| 59 | 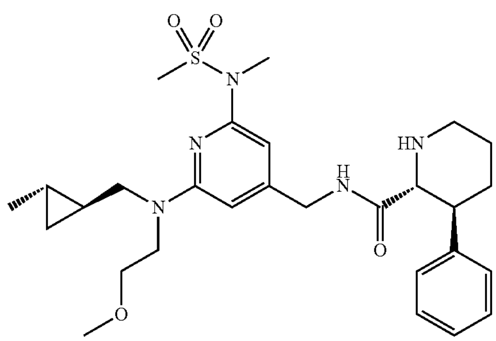 | 543.73 | 544 | TRANS SS, TRANS RS or SR | (2R,3S)-N-({2-((2-methoxyethyl){[(1S,2S)-2-methylcyclopropyl]methyl]amino)-6-[methyl(methylsulfonyl)amino]pyridin-4-yl}methyl)-3-phenylpiperidine-2-carboxamide |
| 60 | 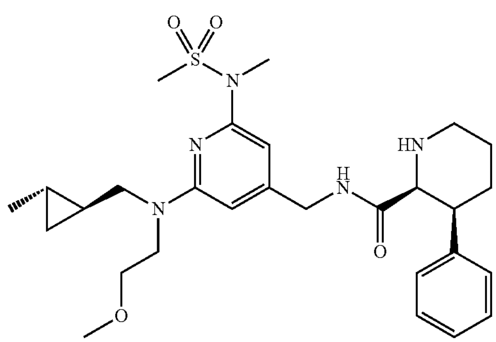 | 543.73 | 544 | TRANS SS, CIS RR or SS | (2S,3S or 2R,3R)-N-({2-((2-methoxyethyl){[(1S,2S)-2-methylcyclopropyl]methyl}amino)-6-[methyl(methylsulfonyl)amino]pyridin-4-yl}methyl)-3-phenylpiperidine-2-carboxamide |

TABLE 5-continued

Pyridylamine Compounds
The following examples were prepared in an analogous manner to examples 46-49 using intermediates of type 3A.2b and related.

| EX | Structure | Parent MW | MS M+H | Stereochemistry | IUPAC NAME |
|---|---|---|---|---|---|
| 61 | 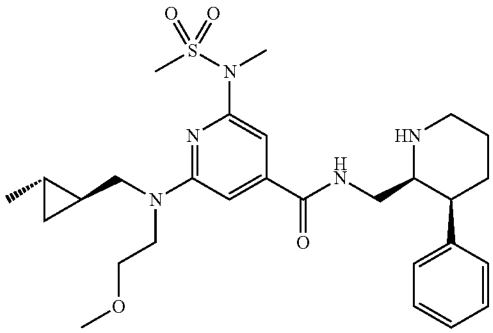 | 543.73 | 544 | TRANS SS, CIS RR or SS | 2-((2-methoxyethyl){[(1S,2S)-2-methylcyclopropyl]methyl}amino)-6-[methyl(methylsulfonyl)amino)-N-{(2S,3S or 2R,3R)-3-phenylpiperidin-2-yl]methyl}isonicotinamide |
| 62 | 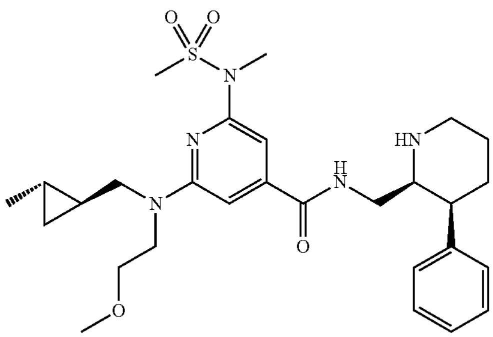 | 543.73 | 544 | TRANS SS, CIS RR or SS | 2-((2-methoxyethyl){[(1S,2)-2-methylcyclopropyl]methyl}amino)-6-[methyl(methylsulfonyl)amino]-N-{[(2S,3S or 2R,3R)-3-phenylpiperidin-2-yl]methyl}isonicotinamide |

The following abbreviations are used throughout the text:

Me: methyl
Et: ethyl
Bu: butyl
t-Bu: tert-butyl
i-Bu: iso-butyl
Pr: propyl
i-Pr: iso-propyl
Ar: aryl
Ph: phenyl
Bn: benzyl
Cbz: carbobenzyloxy
Boc: tert butyloxycarbonyl
TFA: trifluoro acetic acid
THF: tetrahydrofuran
EDC: 1-ethyl-3-(3-dimethyllaminopropyl)carbodiimide
Ac: acetyl
aq: aqueous
rt: room temperature
h: hours
min: minutes

What is claimed is:

1. A compound of formula (II):

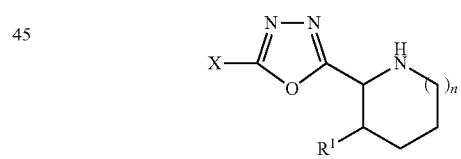

wherein n is 1;

R$^1$ is phenyl,
  wherein said phenyl R$^1$ group is unsubstituted or substituted with one or more groups independently selected from the group consisting of:
  (a) halo,
  (b) —C$_{1-10}$ alkyl, wherein said alkyl is optionally substituted with halogen,
  (c) —OH,
  (d) —CN,
  (e) —O—C$_{1-10}$ alkyl,
  (f) —C$_{3-12}$ cycloalkyl, and
  (g) —NR$^A$R$^B$;

wherein R$^A$ and R$^B$ are selected from the group consisting of
(i) hydrogen,
(ii) —C$_{1-10}$ alkyl, and
(iii) —C$_{1-10}$ alkyl-C$_{6-10}$ aryl;

X is selected from the group consisting of

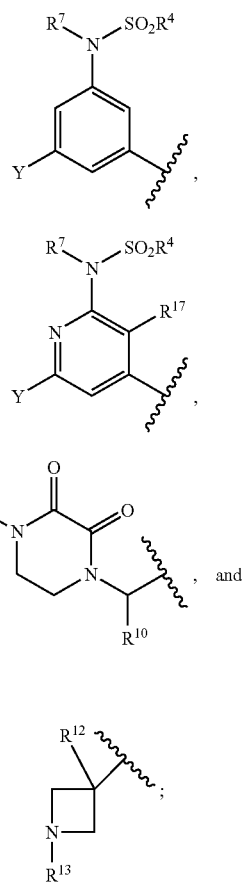

Y is selected from the group consisting of
(1) —NR$^5$R$^6$,
(2) —C(=O)—NR$^5$R$^6$, (3)

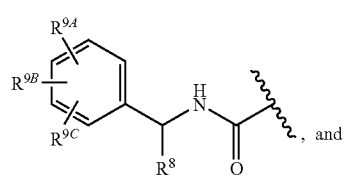

(4) halogen;

R$^4$ is selected from the group consisting of
(1) —C$_{1-10}$ alkyl;

R$^7$ is selected from the group consisting of
(1) hydrogen, and
(2) —C$_{1-10}$ alkyl;

R$^5$ and R$^6$ are independently selected from the group consisting of
(1) hydrogen,
(2) —C$_{1-10}$ alkyl,
and
(4) —C$_{1-10}$ alkyl-C$_{3-12}$ cycloalkyl,
wherein said alkyl or cycloalkyl R$^5$ or R$^6$ group is optionally independently substituted
with one or more groups independently selected from the group consisting of:
(a) halo,
(b) —OH,
(c) —CN,
(d) —C$_{1-10}$ alkyl
(e) —C$_{3-12}$ cycloalkyl,
(f) —O—C$_{1-10}$ alkyl,
(g) heteroaryl, wherein said heteroaryl is optionally substituted with halogen;
(h) phenyl,
(i) —NR$^A$R$^B$, and
(j) —C(=O)—NR$^A$R$^B$, and
(k) —C(=O)—OH,
or R$^5$ and R$^6$ are joined together with the nitrogen atom to which they are attached to
form a 4-6 membered ring, which is optionally substituted with one or more groups independently selected from the group consisting of:
(a) —C$_{1-10}$ alkyl,
(b) —C$_{2-10}$ alkenyl, and
(c) —C$_{2-10}$ alkynyl,
wherein said alkyl, alkenyl and alkynyl is optionally substituted with one or more groups independently selected from the group consisting of:
(i) halo,
(ii) —OH,
(iii) —CN,
(iv) —O—C$_{1-10}$ alkyl, and
(v) —C$_{3-12}$ cycloalkyl, R$^{10}$ is phenyl;

R$^{11}$ is selected from the group consisting of
(1) hydrogen, and
(2) —C$_{1-10}$ alkyl;

R$^{12}$ is selected from the group consisting of
(1) hydrogen, and
(2) —C$_{1-10}$ alkyl;

R$^{13}$ is selected from the group consisting of
(1) C(=O)—R$^{16}$,
wherein R$^{16}$ is selected from the group consisting of
(a) —C$_{1-10}$ alkyl,
(b) —C$_{3-12}$ cycloalkyl,
(c) —(CH$_2$)$_n$-phenyl,
(d) —C$_{2-10}$ alkenyl,
(e) —C$_{2-10}$ alkynyl, or
(f) heteroaryl,
wherein said alkyl, alkenyl and alkynyl R$^{16}$ moiety is optionally substituted with one or more
(i) halo,
(ii) —OH,
(iii) —CN,
(iv) —O—C$_{1-10}$ alkyl, or
(v) —C$_{3-12}$ cycloalkyl,
and said cycloalkyl, heteroaryl and phenyl R$^{16}$ moiety is optionally substituted with one or more
(i) halo,
(ii) —C$_{1-10}$ alkyl,
(iii) —OH,
(iv) —CN, (v) —C$_{3-12}$ cycloalkyl, or (vi) —O—C$_{1-10}$ alkyl, (vii) heteroaryl;

R$^8$ is C$_{1-10}$ alkyl, wherein said alkyl is optionally substituted with one or more halogen;

R$^{9A}$, R$^{9B}$ and R$^{9C}$ are independently selected from the group consisting of (1) hydrogen, (2) halogen, (3) —C$_{1-10}$ alkyl, (4) —OH, (5) —CN, (6) —C$_{3-12}$ cycloalkyl, and (7) —O—C$_{1-10}$ alkyl;

R$^{17}$ is selected from the group consisting of (1) hydrogen, and (2) Cl;

and pharmaceutically acceptable salts thereof, and individual enantiomers and diastereomers thereof.

2. A compound of claim 1, wherein R$^1$ is phenyl, optionally substituted with one or more halo.

3. A compound of claim 1, wherein R$^1$ is phenyl.

4. A compound of claim 1, wherein the compound of formula (II) is a compound of formula (IIA)

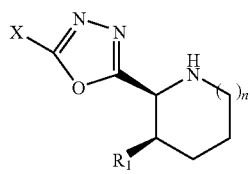

(IIA)

and pharmaceutically acceptable salts thereof, and individual enantiomers and diastereomers thereof.

5. A compound of claim 1, or a pharmaceutically acceptable salt thereof, wherein said compound is selected from the group consisting of:

| EX | Structure |
| --- | --- |
| 50 | 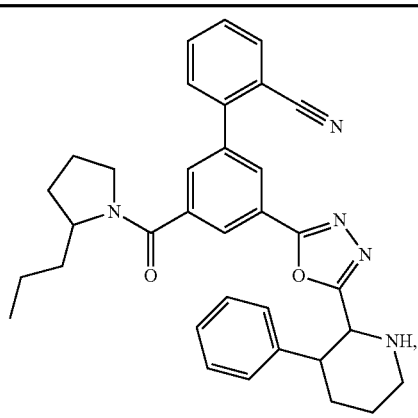 |
| 51 | 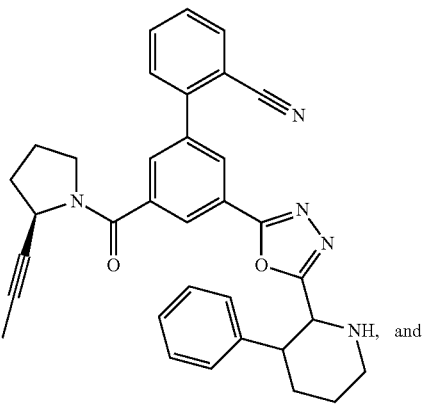 |
| 52 | 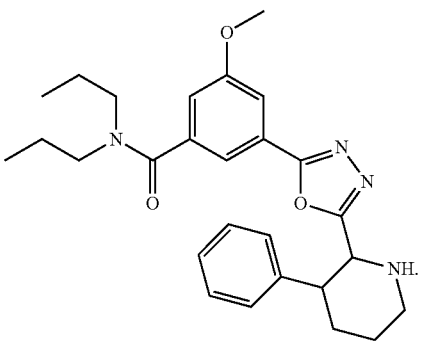 |

6. A compound of claim 3, wherein X is

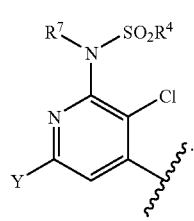

7. A compound of claim 6, wherein R$^7$ is C$_1$-C$_{10}$ alkyl; and Y is

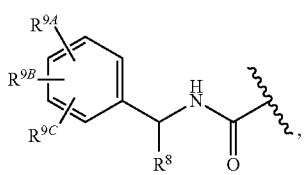

wherein R$^8$ is C$_{1-10}$ alkyl; R$^{9A}$ is halogen; R$^{9B}$ is H; and R$^{9B}$ is H.

8. A compound of claim 6, or a pharmaceutically acceptable salt thereof, wherein said compound is selected from the group consisting of:

| EX | Structure |
|---|---|
| 49 | 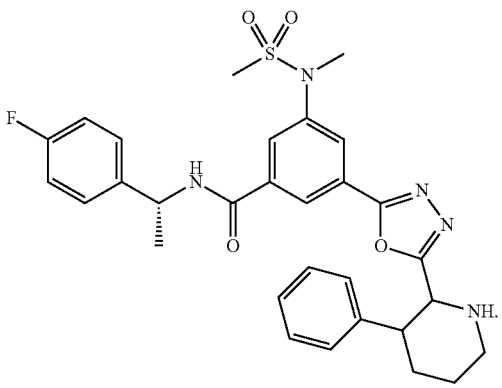 |

9. A compound of claim 3, wherein X is

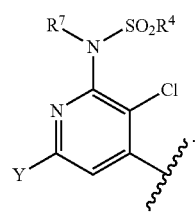

10. A compound of claim 9, wherein Y is NR⁵R⁶.
11. A compound of claim 10, wherein R⁵ and R⁶ are each independently selected from the group consisting of:
(1) hydrogen,
(2) —C$_{1-10}$ alkyl, and
(3) —C$_{1-10}$ alkyl-C$_{3-12}$ cycloalkyl,
  wherein said alkyl or cycloalkyl R⁵ or R⁶ group is optionally substituted with one or more groups independently selected from the groups consisting of:
  (a) halo,
  (b) —OH,
  (c) —C$_{1-10}$ alkyl, and
  (d) —O—C$_{1-10}$ alkyl.

12. A compound of claim 10, or a pharmaceutically acceptable salt thereof, wherein said compound is selected from the group consisting of:

| EX | Structure |
|---|---|
| 20 | 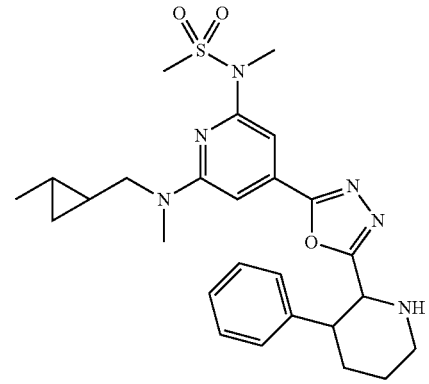 |
| 21 | 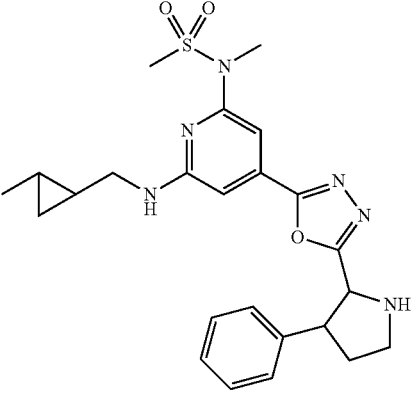 |
| 22 | 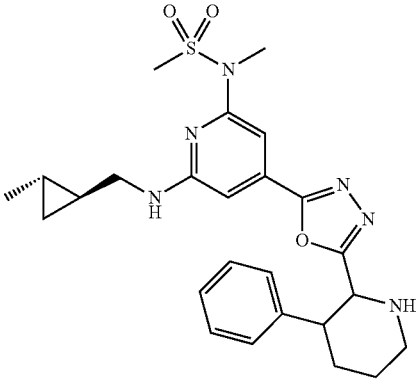 |
| 23 | 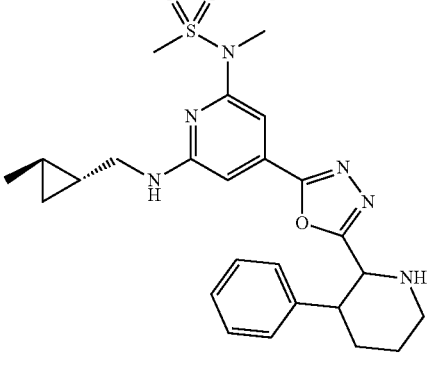 |
| 24 | 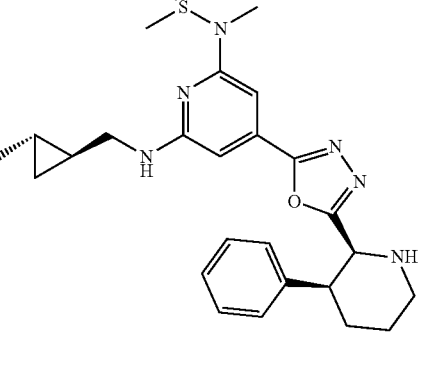 |

-continued

| EX | Structure |
|---|---|
| 25 | 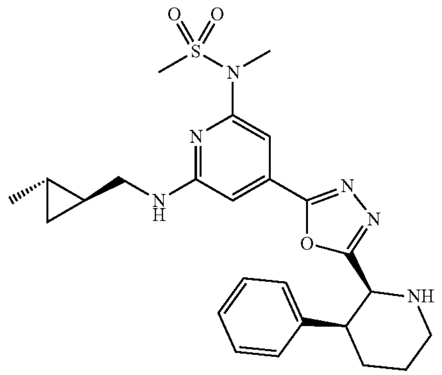 |
| 26 | 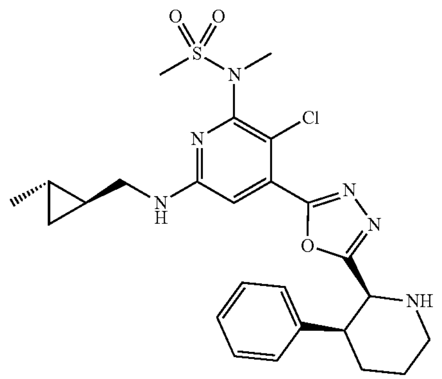 |
| 27 | 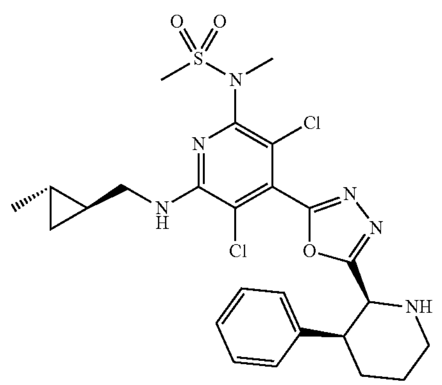 |
| 28 | 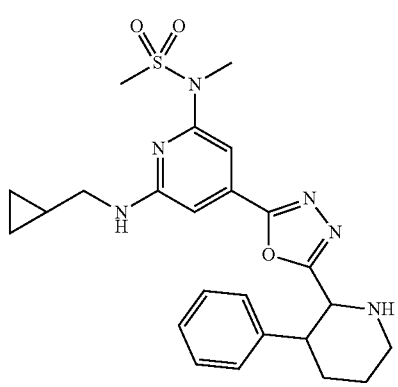 |
| 29 | |
| 30 | |
| 31 | |
| 32 | |

-continued
| EX | Structure |
|---|---|
| 33 | 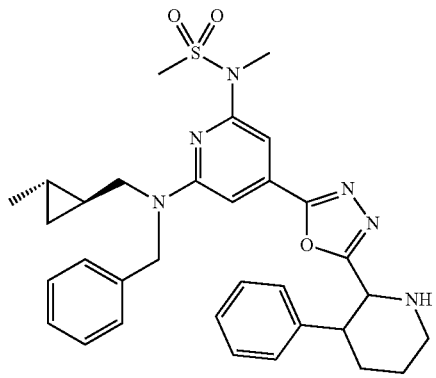 |
| 34 | 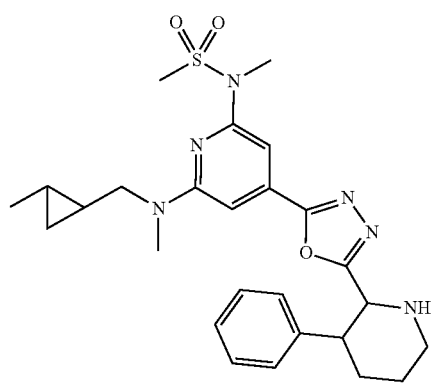 |
| 35 | 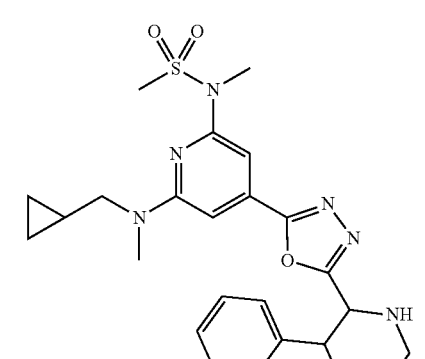 |
| 36 | 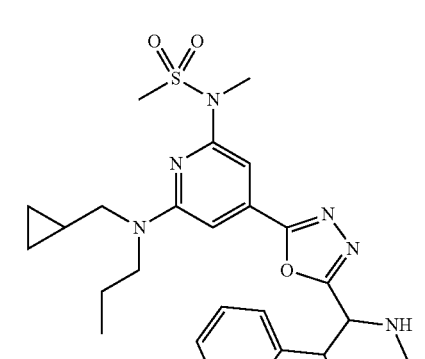 |
-continued
| EX | Structure |
|---|---|
| 37 | 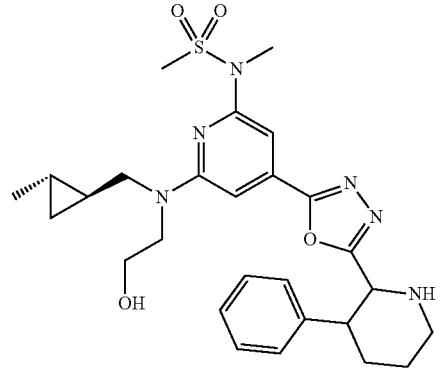 |
| 38 | 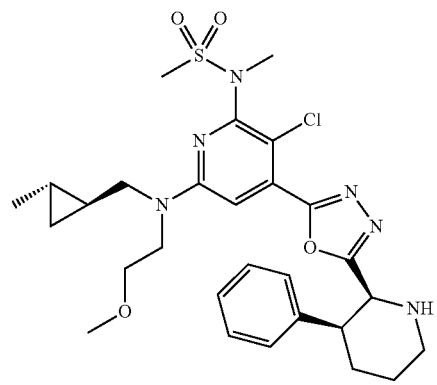 |
| 39 | 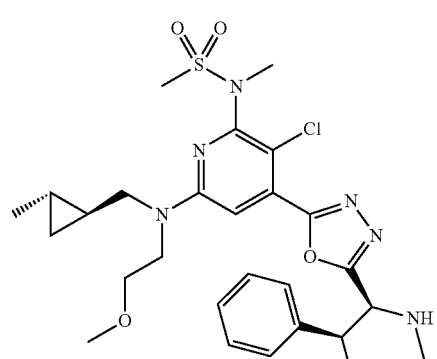 |
| 40 | 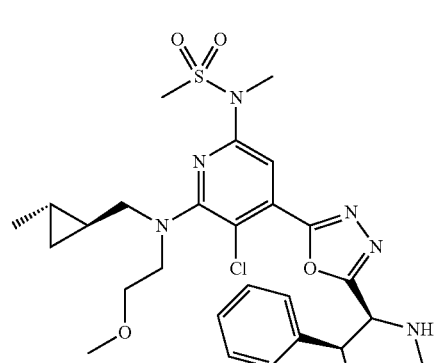 |

79
-continued
| EX | Structure |
|---|---|
| 41 | 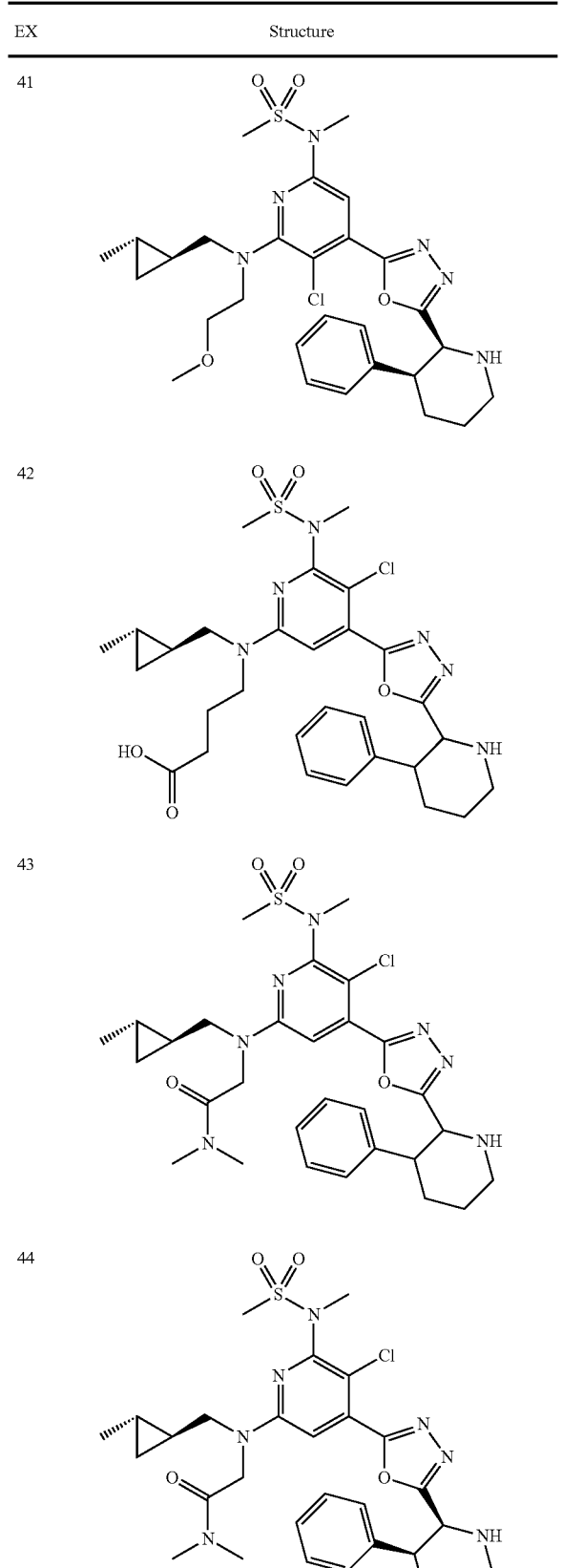 |
| 42 | 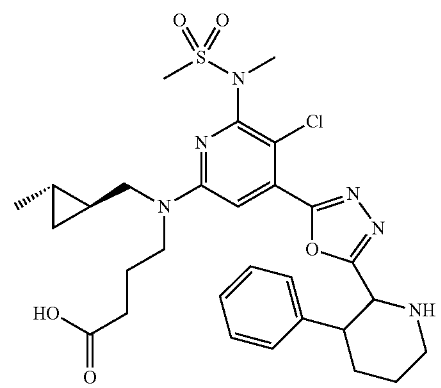 |
| 43 | 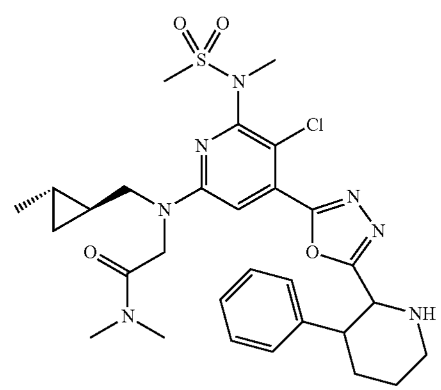 |
| 44 | 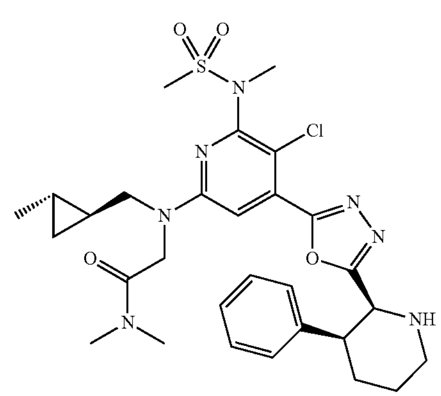 |
80
-continued
| EX | Structure |
|---|---|
| 45 | 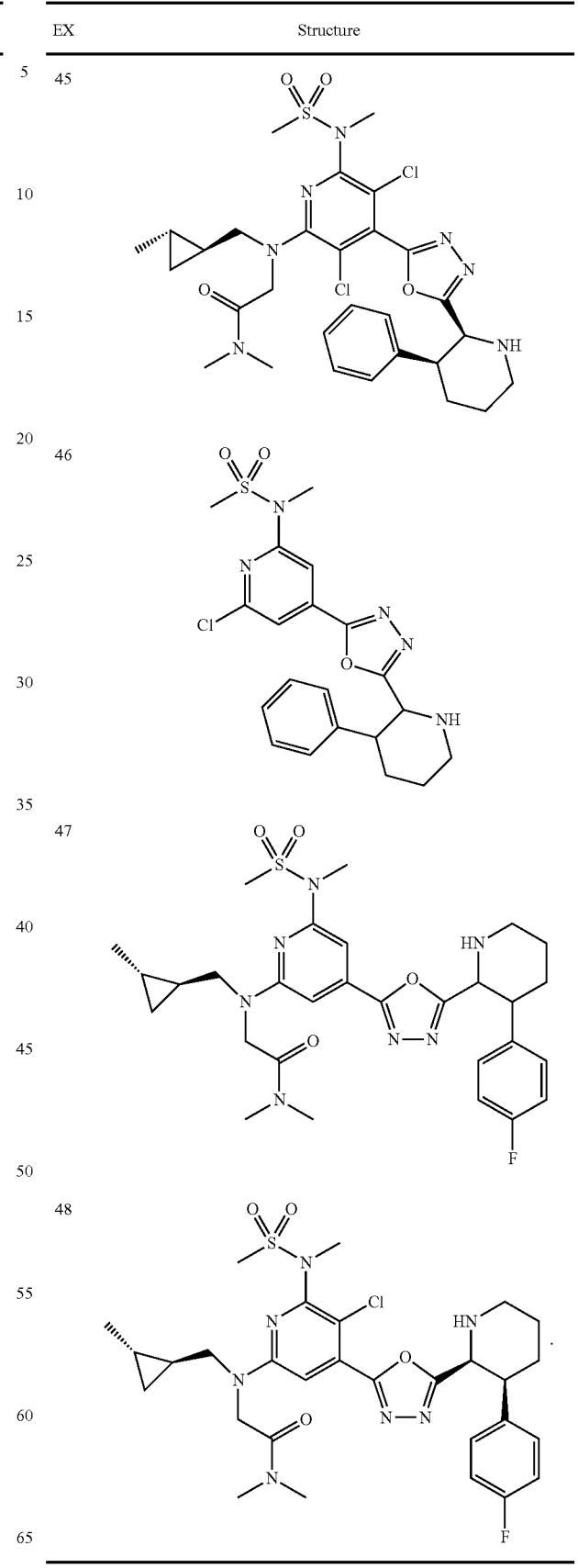 |
| 46 | 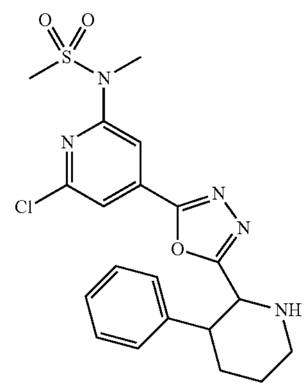 |
| 47 | 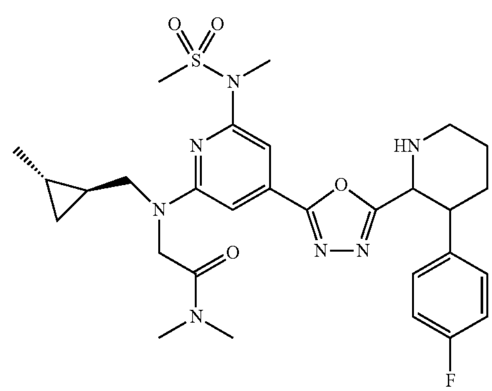 |
| 48 | 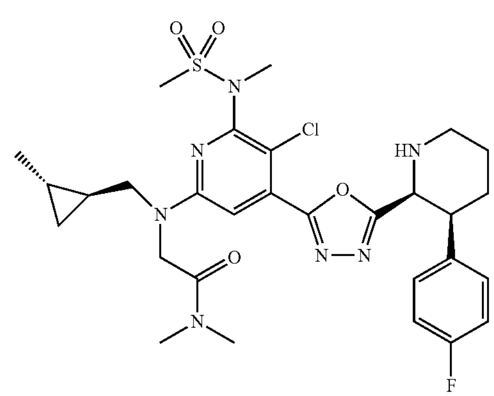 |

13. A compound of claim 3, wherein X is:

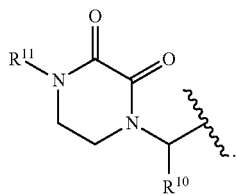

14. A compound of claim 13, wherein $R^{10}$ is phenyl; and $R^{11}$ is —$C_1$-$C_{10}$ alkyl.

15. A compound of claim 14, or a pharmaceutically acceptable salt thereof, wherein said compound is selected from the group consisting of:

| EX | Structure |
|---|---|
| 15 | 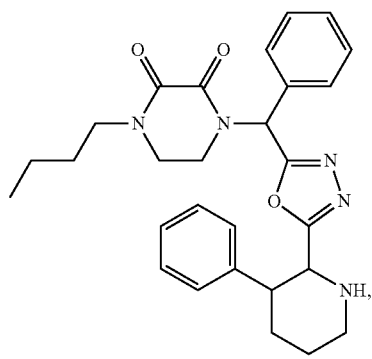 |
| 16 | 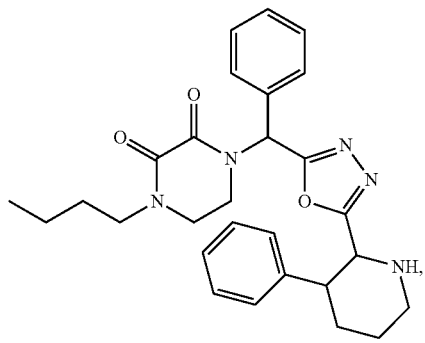 |
| 17 | 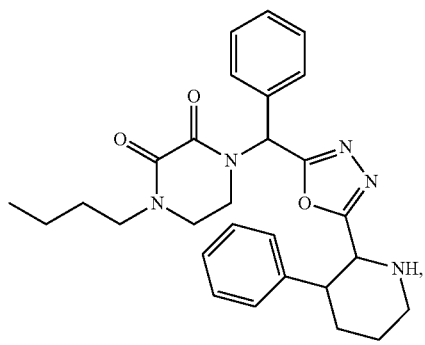 |

-continued

| EX | Structure |
|---|---|
| 18 | 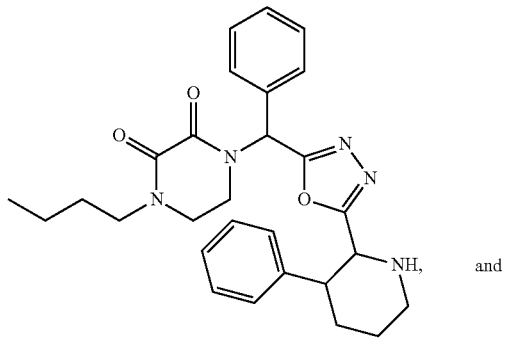 and |
| 19 | 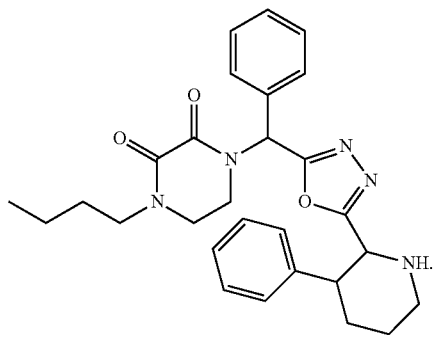 |

16. A compound of claim 3, wherein X is:

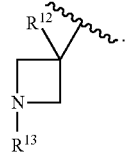

17. A compound of claim 16, wherein $R^{12}$ is selected from the group consisting of H and —$C_1$-$C_{10}$ alkyl; and $R^{13}$ is —C(=O)—$R^{16}$.

18. A compound of claim 16, or a pharmaceutically acceptable salt thereof, wherein said compound is selected from the group consisting of:

| EX | Structure |
|---|---|
| 1 | 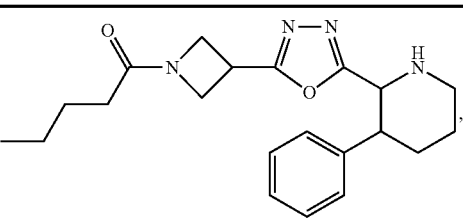 |

-continued

| EX | Structure |
|----|-----------|
| 2 | 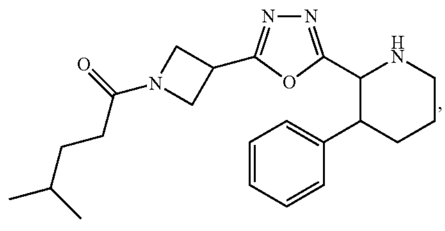 |
| 3 | 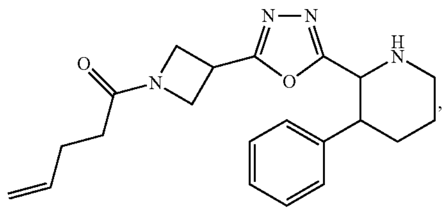 |
| 4 | 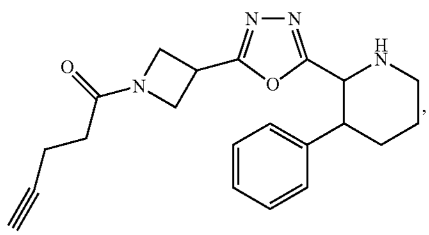 |
| 5 | 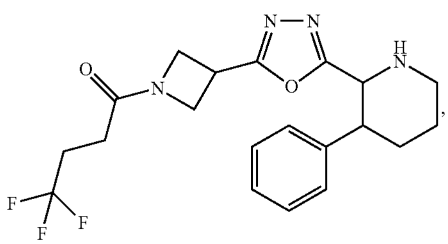 |
| 6 | 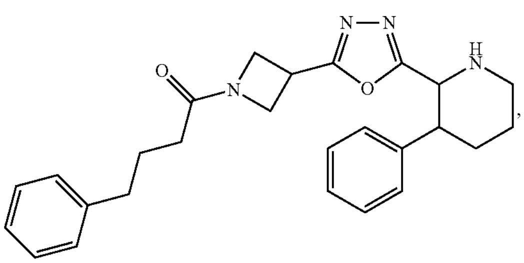 |
| 7 | 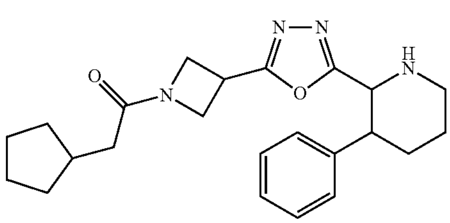 |
| 8 | |
| 9 | |
| 10 | |
| 11 | |
| 12 | |
| 13 | , and |

| EX | Structure |
|----|-----------|
| 14 | 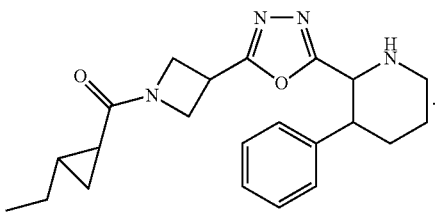 |

19. A pharmaceutical composition comprising a therapeutically effective amount of a compound of claim 1, or a pharmaceutically acceptable salt thereof, and a pharmaceutically acceptable carrier.

20. A method of treating Alzheimer's disease in a patient in need thereof, comprising administering to the patient a therapeutically effective amount of a compound of claim 1, or a pharmaceutically acceptable salt thereof, and a pharmaceutically acceptable carrier.

21. A method for the manufacture of a medicament for treating Alzheimer's Disease, comprising combining a compound of any of the embodiments of claim 1 or a pharmaceutically acceptable salt thereof, with a pharmaceutical carrier or diluent.

* * * * *